US009144408B2

(12) United States Patent
Shahar et al.

(10) Patent No.: US 9,144,408 B2
(45) Date of Patent: Sep. 29, 2015

(54) COLLIMATORS FOR SCAN OF RADIATION SOURCES AND METHODS OF SCANNING

(71) Applicant: General Electric Company, Schenectady, NY (US)

(72) Inventors: Arie Shahar, Moshav Magshimim (IL); Eliezer Traub, Ramat-Gan (IL); Floribertus P. M. Heukensfeldt Jansen, Ballston Lake, NY (US)

(73) Assignee: General Electric Company, Schenectady, NY (US)

( * ) Notice: Subject to any disclaimer, the term of this patent is extended or adjusted under 35 U.S.C. 154(b) by 293 days.

(21) Appl. No.: 13/732,080

(22) Filed: Dec. 31, 2012

(65) Prior Publication Data

US 2014/0138556 A1    May 22, 2014

Related U.S. Application Data

(60) Provisional application No. 61/728,673, filed on Nov. 20, 2012.

(51) Int. Cl.
*G21K 1/02* (2006.01)
*A61B 6/03* (2006.01)
*G01T 1/164* (2006.01)
*A61B 6/00* (2006.01)

(52) U.S. Cl.
CPC ............... *A61B 6/037* (2013.01); *A61B 6/4291* (2013.01); *G01T 1/1648* (2013.01); *G21K 1/02* (2013.01)

(58) Field of Classification Search
CPC ........................................................ G21K 1/02
USPC ................................ 250/363.1; 378/147, 150
See application file for complete search history.

(56) References Cited

U.S. PATENT DOCUMENTS

| 6,353,227 | B1 * | 3/2002 | Boxen .................... 250/363.1 |
| 7,339,176 | B2 * | 3/2008 | El-Hanany et al. ...... 250/370.09 |
| 7,663,111 | B2 | 2/2010 | Shahar et al. |
| 2002/0175289 | A1 * | 11/2002 | Soluri et al. ............... 250/363.1 |
| 2007/0221853 | A1 * | 9/2007 | Joung ...................... 250/363.09 |
| 2008/0073599 | A1 | 3/2008 | Vija |
| 2010/0310037 | A1 * | 12/2010 | Wang et al. ..................... 378/6 |
| 2011/0019801 | A1 * | 1/2011 | Eichenseer et al. ........... 378/147 |
| 2012/0305781 | A1 * | 12/2012 | Jansen et al. ............. 250/363.04 |
| 2013/0077738 | A1 * | 3/2013 | Kreisler et al. .................... 378/7 |

FOREIGN PATENT DOCUMENTS

| JP | 54102184 A | * | 8/1979 |
| JP | 2000199750 A | * | 7/2000 |

* cited by examiner

*Primary Examiner* — Christine Sung
(74) *Attorney, Agent, or Firm* — Dean D. Small; The Small Patent Law Group, LLC

(57) ABSTRACT

Collimators for two-dimensional scans of a radiation sources and methods of scanning are provided. One system includes a scan unit for scanning and collecting ionizing radiation emitted from a radiation emitting object is provided. The scan unit includes an array of at least one pixelated radiation detector having an imaging surface including a two-dimensional (2D) array of pixels. The scan unit also includes a collimator positioned between the radiation detector and the radiation emitting object, with the collimator including a 2D array of columns having openings and septa forming bores, wherein the columns are arranged in groups along rows of the 2D array of columns and the bores within one of the groups have a different aspect ratios than the bores in another one of the groups.

21 Claims, 18 Drawing Sheets

COLLIMATORS FOR SCAN OF RADIATION SOURCES AND METHODS OF SCANNING

CROSS REFERENCE TO RELATED APPLICATIONS

This application claims priority to and the benefit of the filing date of U.S. Provisional Application No. 61/728,673 filed Nov. 20, 2012, the subject matter of which is herein incorporated by reference in its entirety.

BACKGROUND OF THE INVENTION

The subject matter disclosed herein relates generally to the detection of ionizing radiation, such as gamma-ray and X-ray radiation, and more particularly to scanning systems and methods of radiation detection, such as for medical diagnosis, using variable collimators, including Single Photon Emission Computed Tomography (SPECT).

Different scanning methods are known for use in detecting ionizing radiation, such as systems that use variable collimators, for example, adaptive collimators for Nuclear Medicine (NM) imaging. Some known methods of three dimensional (3D) image reconstruction use multiple image-acquisitions with different collimations of the imaging-collimator, such as by changing the collimation of the imaging-collimator. These systems use forward looking variable collimators constructed from multiple collimation elements where each collimation element may be varied and may produce multiple corresponding viewing-angles with a primary axis that is normal to imaging planes produced by detectors. These imaging planes are behind the collimators and are arranged to receive the radiation emitted from an imaged object via the collimators. The structures of the collimators and collimation elements are designed to reduce or avoid crosstalk of radiation between the collimation elements, for example, to prevent or reduce the likelihood of gamma rays passing through the gap of one septum into another collimator aperture.

The collimation variation in these systems is produced by changing the collimator height using means that move along a direction that is normal to the imaging plane while there is no relative movement between the collimator and the radiation detectors in a lateral direction, which is parallel to the imaging surface of the radiation detectors. However, in some situations, such a configuration may not be easy to implement and may increase the complexity of the system.

Additionally, the different viewing angles produced by the variable collimation elements are included in each other such that each viewing angle contains all the viewing angles that are smaller than this viewing angle. As a result, acquisition of multiple images using variable collimators of conventional systems creates a significant redundancy of information in which the same information appearing in one image appears in another image as well. In some of the images, the repeated information is the major information and only a small fraction of the information in these images is new information that does not appear in other images.

In order to increase the sensitivity of the imaging system, each of the multiple images acquired in different collimation of the imaging-collimator includes the imaged region. This imaged region is on and in the imaged object and is significantly larger than the size of the desired spatial resolution. The reconstruction of the image within the desired spatial resolution is produced by various image-reconstruction methods which include intensive mathematical calculations based on multiple equations that use image data from the multiple images. For example, in some systems, the number of images acquired for reconstructing a SPECT image times the number of pixels in each image is equal to the number of virtual voxels into which the imaged object is to be divided. Accordingly, the large size of the imaged region in each acquired image and the large number of acquired images that are needed for the 3D image reconstruction does not allow for selecting only images that have no information redundancy.

Thus, the reconstruction of images using some known systems and methods includes repetitive information that is summed with newly acquired information. As a result, reconstructed images may have reduced image quality and may also include reconstruction artifacts.

BRIEF DESCRIPTION OF THE INVENTION

In accordance with one embodiment, a scan unit for scanning and collecting ionizing radiation emitted from a radiation emitting object is provided. The scan unit includes an array of at least one pixelated radiation detector having an imaging surface including a two-dimensional (2D) array of pixels. The scan unit also includes a collimator positioned between the radiation detector and the radiation emitting object, with the collimator including a 2D array of columns having openings and septa forming bores, wherein the columns are arranged in groups along rows of the 2D array of columns and the bores within one of the groups have a different aspect ratio than the bores in another one of the groups.

In accordance with another embodiment, a scan unit for scanning and collecting ionizing radiation emitted from a radiation emitting object is provided. The scan unit includes a plurality of scanning elements and a variable collimation system, wherein for each of a plurality of collimation and directional settings of the plurality of scanning elements there is a corresponding two-dimensional (2D) scanning angle for acquiring data to generate an image that is different for different scanning angles.

In accordance with yet another embodiment, a method for scanning and collecting ionizing radiation emitted from an object using a scan unit having an array of at least one pixelated radiation detector with an imaging surface including a two-dimensional (2D) array of pixels is provided. The method includes configuring a collimator to be positioned between the radiation detector and the radiation emitting object, wherein the collimator includes a 2D array of columns having openings and septa forming bores and the columns are arranged in groups along rows of the 2D array of columns, with the bores within one of the groups having a different aspect ratios than the bores in another one of the groups. The method also includes controlling the collimator to move linearly, by scanning steps, in a direction along the lines of the array of the columns and parallel to the imaging surface of the detector for changing relative positions between the groups of the columns and the pixels. In some embodiments, the entire array is scanned.

DETAILED DESCRIPTION OF THE INVENTION

Figure 1:
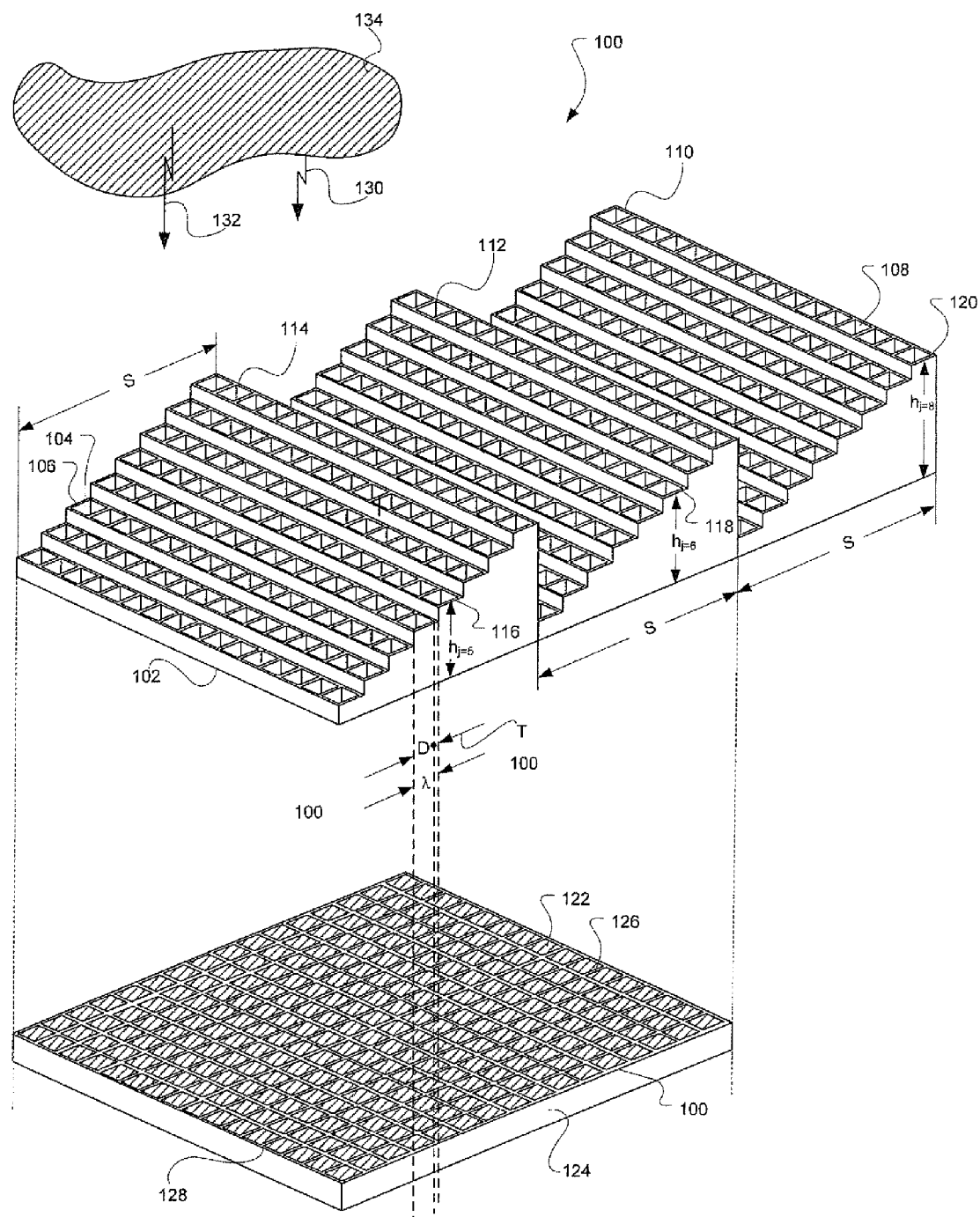
FIG. 1 is a schematic perspective view illustration of a scan unit in accordance with one embodiment.

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image, as well as data representing estimated activity distribution (e.g., a kinetic curve). However, many embodiments generate, or are configured to generate, at least one viewable image.

Various embodiments provide systems and methods for collimation for two-dimensional (2D) scanning for radiation detectors, such as Single Photon Emission Computed Tomography (SPECT) detectors. However, the various embodiments may be implemented in different types of detectors, such as radiation detectors for detecting ionizing radiation (e.g., gamma-ray or X-ray radiation). In particular, some embodiments provide a displacing collimator for non-forward wide-angle and high sensitivity 2D scanning of radiation detectors.

At least one technical effect of various embodiments is acquiring images with high sensitivity and/or allowing high quality image-reconstruction of an imaged object. At least one other technical effect of various embodiments is providing a scan system having an imaging-collimator including variable collimation elements.

Various embodiments provide a scan system having an imaging-collimator including variable collimation elements. In some embodiments, a scan system is provided having an imaging-collimator capable of producing variable collimation by lateral displacement. Also, a scan system may be provided that includes a pixelated detector array in which the number of collimation elements in the radiation scanning-unit is larger than the number of pixels in the pixelated detector array. In various embodiments, the radiation scan unit has collimation elements that may include a pinhole plate.

The scan system of one or more embodiments is configured to acquire multiple images of the imaged object that are substantially different from each other for allowing high quality image-reconstruction of the imaged object. In some embodiments, a radiation scan unit is provided having imaging-elements with variable collimation elements, wherein for each scan setting of the scan unit, there is a corresponding image of the imaged object acquired by the pixelated detector via the imaging scan unit and wherein the image is substantially different for different scan settings.

In other embodiments, an angular scanning system is provided having imaging elements including scanning elements, wherein for each collimation and directional setting of the angular scanning system, there is a corresponding two-dimensional angular scan for producing a corresponding image that is substantially different for different scanning angles.

Also, in some embodiments, a collimator is provided that converts a lateral scan into a 2D radiation scan (including variable collimation).

FIG. 1 is a schematic perspective-view illustration of radiation scan unit 100 (also referred to as a radiation scanning unit 100) including a laterally movable collimator 102 having an array of columns, illustrated as square hollow-columns 108 that include openings 104 separated by septa 106. In this embodiment, the collimator 102 includes three periodic structures 110, 112 and 114 having periodic length S. Each of the periodic structures 110, 112 and 114 contains a set of eight groups of columns 108. However, additional or fewer columns 108 may be provided. Each group of columns 108 has a height $h_j$ where all the columns within each group have the same height $h_j$ and the height of the columns in each group is different from the height of the columns in another group. For example, the columns 116, 118 and 120 of periodic structures 114, 112 and 110 have heights $h_{j=5}$, $h_{j=6}$ and $h_{j=8}$, respectively, where $h_{j=5}$, $h_{j=6}$ and $h_{j=8}$ have different height value.

Each of the columns 116, 118 and 120 is related to another group of columns 108 and thus has different height. The groups of columns 108 are also arranged in rows. For example, the rows that include columns 116, 118 and 120 are three different groups of columns 108 out of the eight groups of columns 108 included in each period S of the periodic structures 110, 112 and 114, respectively. The columns 108 are arranged in a two dimensional (2D) array structure having a two dimensional pitch α. The pitch λ includes the size D of the square openings 104 with the additional thickness T of one of the septa 106.

For clarity of the drawing and for illustrating the 2D array of pixels 122 of the pixelated radiation detector 124, the detector 124 is illustrated as remote from the collimator 102. However, in various embodiments of the radiation scan unit 100, the detector 124 is positioned in close proximity (e.g., adjacent) to the collimator 102. The array of pixels 122 has a 2D pitch that is equal to a 2D pitch α of the collimator 102. In one embodiment, the projections of the openings 104 of the columns 108 and corresponding septa onto the imaging surface 128 of the detector 124 are aligned with the centers of the pixels 122 and the border lines 126 between adjacent pixels 122, respectively.

The collimator 102 may be made of or fabricated from radiation absorbing materials, such as lead (Pb) or tungsten (W). The thickness of the septa 106 is configured to absorb most of the ionizing radiation 130 and 132, such as X-rays and Gamma-rays emitted from the surface and the volume of the radiation emitting object 134, respectively. The radiation source 134 may be a patient body into which radioactive isotopes (tracers) have been injected for the purpose of medical diagnostics, such as for NM applications.

The pixelated detector 124 may be made of or fabricated from semiconductor materials, such as Cadmium Zinc Telluride (CdZnTe or CZT). The detector 124 may be formed from a single plate or may be formed from multiple tiles of semiconductor-detectors that are butted (in an adjacent arrangement) to produce the imaging surface 128. The imaging plane 128 may be formed when the pixels 122 are facing up, but the detector 124 may be used in a configuration when the pixels 122 are facing down as well and as illustrated by FIG. 2.

The radiation scan unit 100 scans the radiation emitting object using the imaging collimator 102 through which part of the radiation 130 and 132 emitted from the radiation emitting object 134 passes and propagates via the columns 108 to be collected by the pixels 122 of the radiation detector 124. The scanning performed by the radiation scan unit 100 including the scan employed to reconstruct images of the radiation emitting object 134, including 3D image reconstruction, such as SPECT reconstruction, is described in more detail below.

Figure 2:
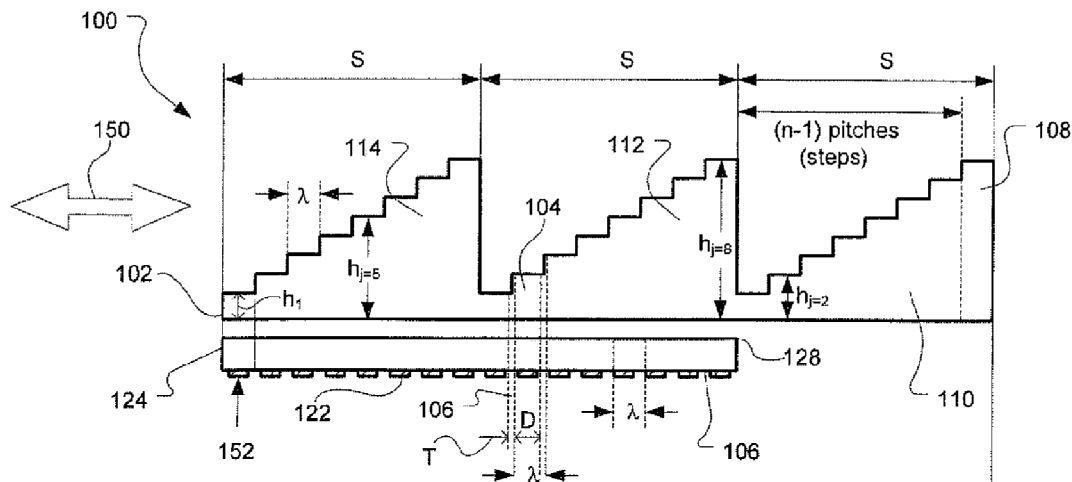
FIGS. 2-4 are schematic side-view illustrations of the scan unit of FIG. 1.
Figure 3:
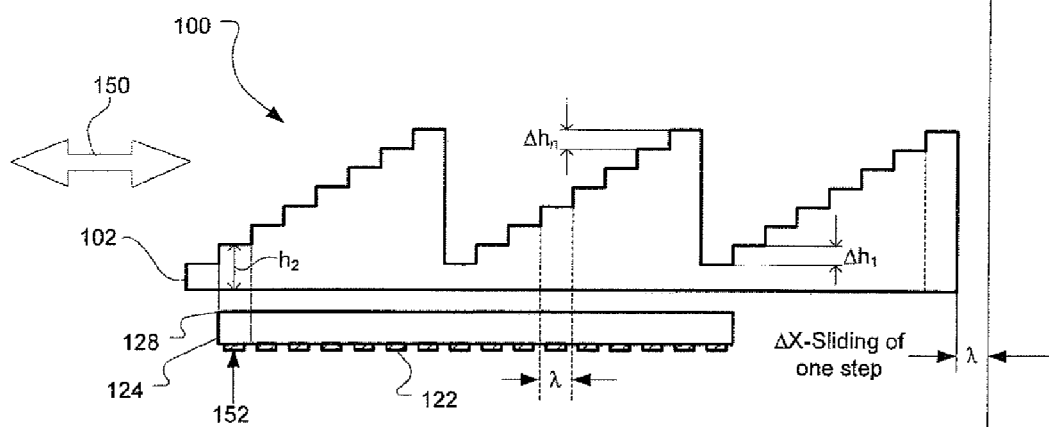
Figure 4:
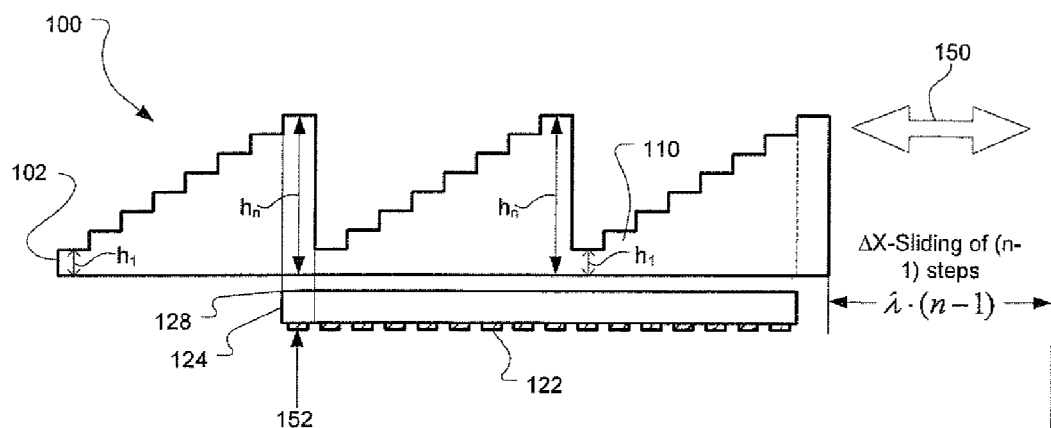

FIGS. 2-4 are schematic side-view illustrations of the scan unit 100 shown in perspective in FIG. 1. The same reference numerals are used for similar features, parts and components in FIGS. 1, 2-4 and other figures described herein. FIGS. 2-4 are different from FIG. 1 as follows: the radiation emitting object 134 of FIG. 1 is not shown in FIGS. 2-4. The radiation detector 124 of FIG. 1 is positioned in FIGS. 2-4 in the vicinity of (or in proximity to) the collimator 102. The detector 124 in FIGS. 2-4 is upside-down relative to the position shown in FIG. 1 to have the pixels 122 facing down. In this case, the imaging surface 128 of the detector 124 is located in the cathode plane of the detector 124. The voxels of the detector 124 are the volumes in the detector 124 that include the pixels 122.

FIG. 2 schematically shows the collimator 102 including the periodic structures 110, 112 and 114 placed above the detector 124 and movable in the lateral directions along arrows 150. As described above for FIG. 1, each of the periodic structures 110, 112 and 114 has a period size S and includes eight groups of columns 108 with a height of the columns 108 the same for the columns belonging to the same group and different for columns belonging to different groups, i.e. each group has columns 108 with different heights $h_j$. The index j is the group index and the height index as well. The columns 108 have a pitch size λ which is equal to the sum of the size D of the openings 104 and the thickness T of the septa 106.

In one embodiment, the columns 108 of the collimator 102 are aligned with the pixels/voxels 122 such that the centers of the openings 104 and the septa 106 of the columns 108 of the collimator 102 are aligned with the centers of the pixels 122 and the border lines 126 (see also FIG. 1) in the imaging plane 128 of the detector 124, respectively. The collimator 102 is movable step by step by mechanical means (not shown) to produce the scan of the scan unit 100. The moving or sliding of the collimator 102 may be accomplished, for example, by motors, manipulators or other means used for mechanical movement or translation. The step size of the scan of collimator 102 along the arrows 150 is equal to the pitch size λ of the collimator 102 and the detector 124. This means that for each step position of the scan, the columns 108 of the collimator 102 are aligned with the pixels 122 as described above.

FIG. 2 shows the scan unit 100 in a scanning position when the periodic structures 112 and 114 are above the detector 124 and the periodic structure 110 is out of the detector 124. For every scan distance S that is equal to the period size of the periodic structures 110, 112 and 114, the scan position repeats itself. This means that there are eight different scanning steps of the collimator 102 in the illustrated embodiment. Since the initial scan position of the collimator 102 is one of these scanning steps, there are seven step positions left to produce the scan of the collimator 102 before the scan will repeat the initial scan position. In general, for a periodic structure having n groups with n different heights of columns 108, there are (n−1) non-repetitive scanning steps.

It should be noted that alternatively the entire array may be scanned, wherein the collimator 102 is fixed to the detector 124 and a "tight pitch helical" scan results in each part of the image scanned with each kind of collimator. In this embodiment, "multiple staircases" are not provided. Also because the collimator 102 is fixed with respect to the detector 124, any sensitivity errors due to alignment issues can be calibrated once.

FIG. 3 schematically illustrates the scan unit 100 after one scanning step relative to the initial scan position shown in FIG. 2. In this scan position, the collimator 102 moves laterally or linearly one step to the left in the direction of the arrows 150 along a displacement distance ΔX that is equal to λ. Since the step size is λ, the same pixel 152 of the pixels 122 of the detector 124 that is aligned with the column 108 having height $h_1$ in FIG. 2, is aligned with the column 108 having height $h_2$ in FIG. 3. It should be noted that the height of the columns 108 above the pixels 152 changes due to the lateral scan of the collimator 102 and exists for all the pixels 122 of the detector 124. The scanning of the scan unit 100 as shown in FIGS. 2 and 3 as explained above is performed for every scan step of the collimator 102 and every pixel 122.

Accordingly, it should be clear that the index j of height $h_j$ of the column 108 above every pixel 122 is increased by one for every scanning step. Since the scan position shown in FIG. 3 is one step after the initial scan position of FIG. 2, the height above the pixel 152, which is $h_1$ in FIG. 2, is $h_2$ in FIG. 3. The scanning operation or principle of the scan can be defined in more general form as follows: the index j of height $h_j$ of the column 108 above every pixel 122 is increased by k for every k scanning steps of the lateral scan of the collimator 102.

For example, the column 108 of FIG. 2 having height $h_5$ will be positioned above the pixel 152 after four lateral scanning steps of the collimator 102. Similarly, the column 108 of FIG. 2 having a height $h_n$ will be positioned above the pixel 152 after (n−1) lateral scanning steps of the collimator 102. The height change between columns related to different groups of the columns 108 can be selected as desired. For example, the height change $\Delta h_8$ between $h_{j=8}$ and $h_{j=7}$ may be equal to or different from the height change $\Delta h_1$ between $h_{j=2}$ and $h_{j=1}$. In general, the height change $\Delta h_1$ between $h_{(1+1)}$ and $h_1$ may be equal to or different from the height change $\Delta h_j$ between $h_{(j+1)}$ and $h_j$.

FIG. 4 illustrates the collimator 102 in a final scan position when the column 108 having height $h_n$ is placed above the pixel 152. In this final scan position, the scanning displacement ΔX of the collimator 102 relative to the initial scan position as shown in FIG. 2 is (n−1) times λ. It can be seen that the column 108 of the periodic structure 110 having height $h_1$ is very asymmetric, i.e. having a height $h_1$ on the right side and a height $h_n$ on the left side. An alternative configuration and more symmetric periodic structure of the periodic structures 110, 112 and 114 is illustrated by the embodiment shown in FIGS. 5-7.

Figure 5:
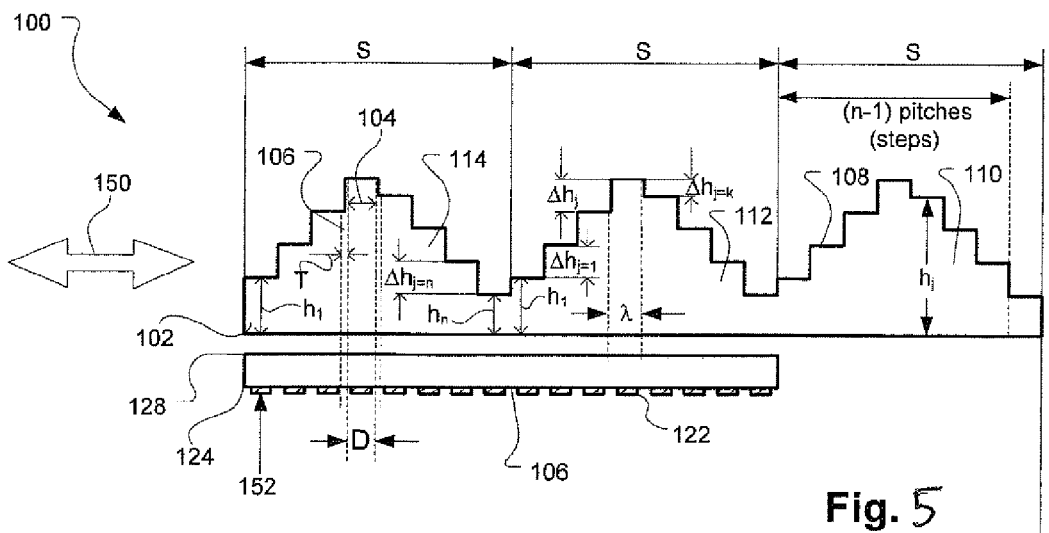
FIGS. 5-7 are schematic side-view illustrations of a scan unit in accordance with another embodiment.
Figure 6:
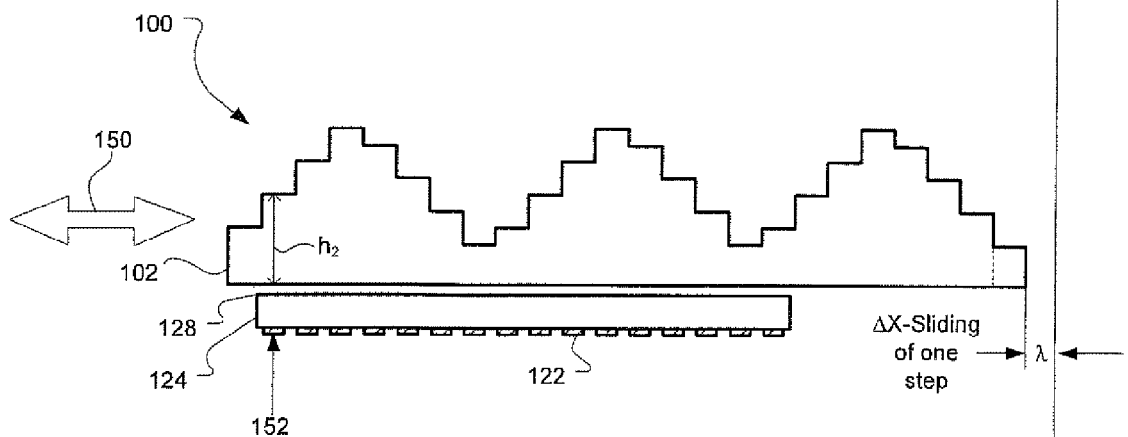
Figure 7:
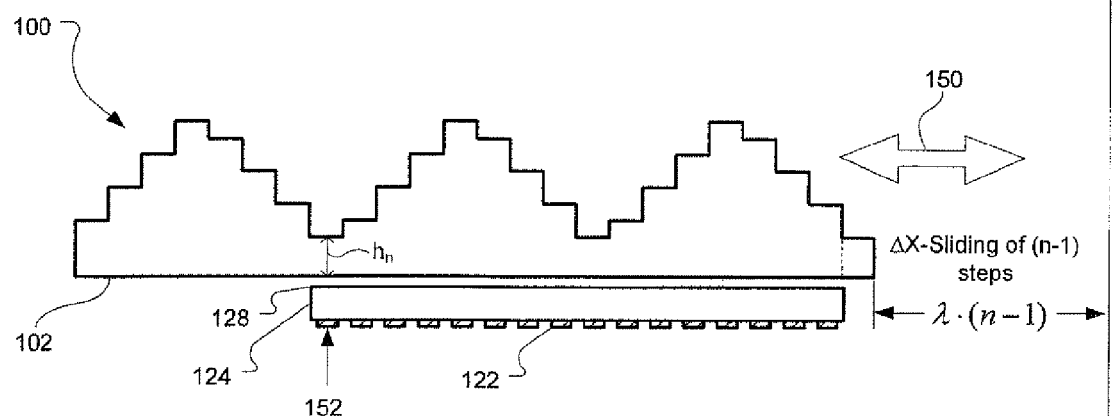

FIGS. 5-7 are schematic side-view illustrations of the scan unit 100 similar to the one illustrated by FIGS. 2-4, except that the groups of columns 108 are arranged more symmetrically in the periodic structures 110, 112 and 114.

In particular, FIG. 5 schematically shows the collimator 102 having the periodic structures 110, 112 and 114, which is placed above the detector 124 and is movable in the lateral directions along the arrows 150. In one embodiment, the columns 108 of the collimator 102 are aligned with the pixels/voxels 122 such that the centers of the openings 104 and the septa 106 of the columns 108 of the collimator 102 are aligned with the centers of pixels 122 and the border lines 126 (see also FIG. 1) in the imaging plane 128 of the detector 124, respectively. The collimator 102 is movable step by step by mechanical means (not shown) to produce the scan of the scan unit 100. Moving or sliding the collimator 102 can be performed, for example, by motors, manipulators or other means used for mechanical movement or translation. The step size of the scan of the collimator 102 along the arrows 150 is equal to the pitch size of the collimator 102 and the detector 124. This means that for each step position of the scan, the columns 108 of the collimator 102 are aligned with the pixels 122 as described above.

FIG. 5 shows the scan unit 100 in a scanning position when the periodic structures 112 and 114 are above the detector 124 and the periodic structure 110 is out of the detector 124. For every scan distance S that is equal to the period size of the periodic structures 110, 112 and 114, the scan position repeats. This means that in the illustrated embodiment, there are eight different scanning steps of the collimator 102. Since the initial scan position of the collimator 102 is one of these scanning steps, there are seven step positions left to produce the scan of the collimator 102 before the scan repeat the initial scan position. In general, for a periodic structure having n groups having n different heights of columns 108, there are (n−1) non-repetitive movements, such that scanning is performed n times and moving n−1 times. The height differences $\Delta h_j = h_{(j+1)} - h_j$, such as height differences $\Delta h_{j=1}$, $\Delta h_{j=k}$ and $\Delta h_{j=n}$ between the columns 108 in the periodic structures 110-114 are selected to produce 8 different heights $h_j$ for eight different groups of columns 108 in the illustrated embodiment. The asymmetric structure of the periodic structures 110-114, as illustrated by FIGS. 2-4, cause the column 108 having height $h_1$ to have sidewalls (the septa 106) with a height $h_{j=n}$ on the left sidewall and with a height $h_1 = 1$ on the right sidewall. The short column 108, such as the one having height $h_j = 1$ crates a collimation with wide solid viewing angle for this column. However in the embodiment of FIGS. 2-4, such a column 108 having height $h_j = 1$ has, on the left a side wall having height of $h_{j=n}$, which limits the wide collimation of this column by narrowing the solid viewing-angle thereof. Accordingly, the groups of columns 108 in the periodic structures 110-114 of FIGS. 5-7 are arranged symmetrically to produce for each column 108 sidewalls (the 106) having heights which are different from each other only by an incremental height step $\Delta h_j$ corresponding to the height difference between adjacent columns 108. Such an arrangement is achieved by positioning the group of columns 108 having the highest height $\Delta h_{j=k-1}$ (k=n/2 when n is an even number and k=(n+/−1)/2 when n is an odd number) near the center of periodic range S of the periodic structures 110-114. The remaining groups of columns 108 are distributed symmetrically about this center when the groups of columns 108 having the most similar heights are positioned symmetrically with respect to the center of the periodic scan range S. In various embodiments, a fixed collimator with different groups of holes/bores is provided for scanning an object (e.g., a patient) relative to the detector such that every part of is viewed by every kind of collimator.

FIG. 6 schematically illustrates the scan unit 100 after one scanning step relative to the initial scan position shown in FIG. 2. In this scan position, the collimator 102 moves laterally one step to the left in the direction of the arrows 150 along a displacement distance ΔX that is equal to λ. Since the step size is λ, the same pixel 152 of the pixels 122 of the detector 124 that is aligned with the column 108 having height $h_1$ in FIG. 5, is aligned with the column 108 having height $h_2$ in FIG. 6. It should be noted that the height of columns 108 above pixels 152 is changed due to the lateral scan of collimator 102 for all pixels 122 of the detector 124. The scanning operation of the scan unit 100 as shown in FIGS. 5 and 6 applies to every scan step of the collimator 102 and the every pixel 122.

Accordingly, it should be clear that the index j of height $h_j$ of the column 108 above every pixel 122 is increased by one for every scanning step. Since the scan position shown in FIG. 6 is one step after the initial scan position of FIG. 5, the height above the pixel 152, which is $h_1$ in FIG. 5, is $h_2$ in FIG. 6. The scanning operation or principle of operation of the scan can be defined in general form as follows: the index j of height $h_j$ of the column 108 above every the pixel 122 is increased by k for every k scanning steps of the lateral scan of the collimator 102.

For example, the column 108 of FIG. 5 having height $h_6$ will be positioned above the pixel 152 after five lateral scanning steps of the collimator 102. Similarly, the column 108 of FIG. 5 having height $h_k$ will be positioned above the pixel 152 after (k-1) lateral scanning steps of the collimator 102. The height change between columns related to different groups of the columns 108 can be selected as desired. For example, the height change $\Delta h_{n=7}$ between $h_{j=8}$ and $h_{j=7}$ may be equal to or different from the height change $\Delta h_1$ between $h_{j=2}$ and $h_{j=1}$. In general, the height change $\Delta h_1$ between $h_{(j+1)}$ and $h_1$ may be equal to or different from the height change $\Delta h_j$ between $h_{(j+1)}$ and N.

FIG. 7 illustrates the collimator 102 in a final scan position when the column 108 having height $h_n$ is placed above the pixel 152. In this final scan position, the scanning displacement $\Delta X$ of the collimator 102 relative to the initial scan position as shown in FIG. 5, is (n−1) times $\lambda$. It can be seen that the column 108 of the periodic structure 110 having height $h_1$ is very close to symmetric, i.e. has height $h_1$ on the right side and height $h_n + \Delta h_n$ on the left side.

Figure 8:
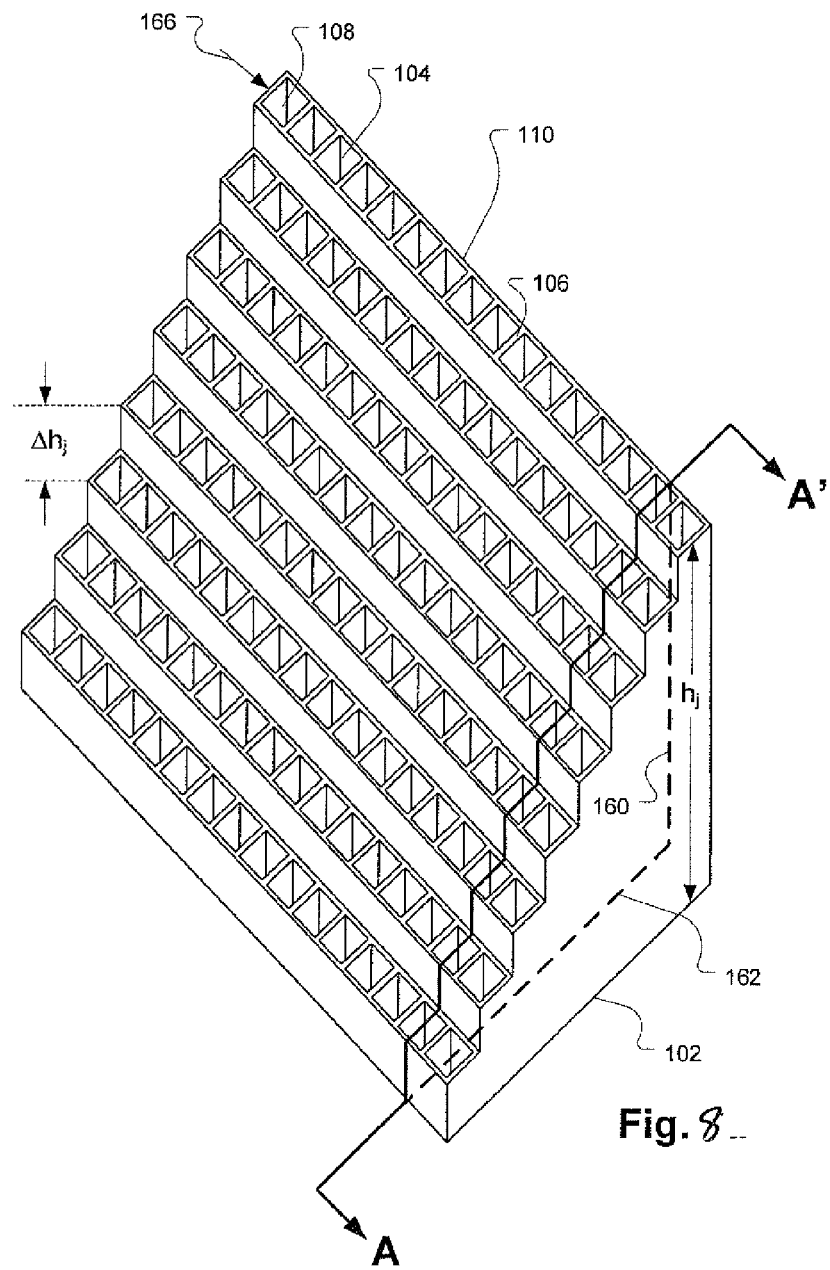
FIG. 8 is a schematic perspective view of a portion of a collimator in accordance with an embodiment.

FIG. 8 is a schematic perspective view of part of the collimator 102 showing one periodic structure 110 of the collimator 102. The collimator 102 includes eight groups of columns 108 arranged along rows 166 of the periodic structure 110 in this embodiment. Each group of columns 108 has a different height $h_j$ and two adjacent groups are different in height by an amount $\Delta h_j$. The columns 108 have square openings 104 and are separated by the septa 106. The stepped line A-A' and the lines 160 and 162 define a cross-section plane along which the periodic structure 110 may be cut to form a side-view cross-section similar to the side-view cross-section illustrated by FIG. 9.

Figure 9:
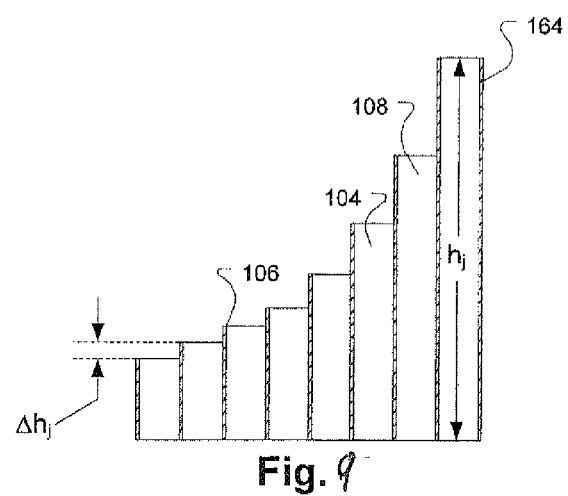
FIG. 9 is a side view cross-section A-A' of the collimator portion illustrated by FIG. 8

FIG. 9 is a side-view cross-section 164 of the periodic structure similar to the periodic structure 110 of FIG. 8. It should be noted that the side-view cross-section 164 may not be proportional to the cross-section of the structure 110 of FIG. 8 that is cut along plane A-A'. To illustrate that the height differences $\Delta h_j$ can be selected as desired, FIG. 9 shows the height differences $\Delta h_j$ between the columns 108 as being different from the height differences $\Delta h_j$ between columns 108 of FIG. 8.

Figure 10:
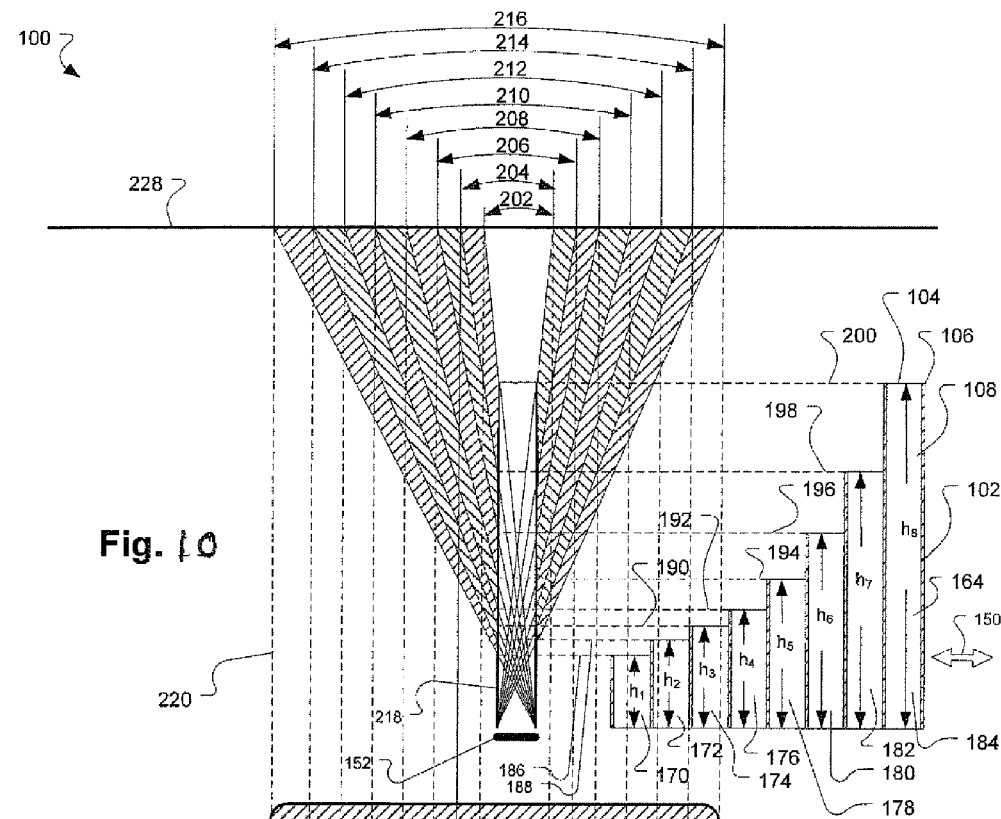
FIG. 10 is a schematic side view illustrating collimated solid viewing angles in accordance with an embodiment.

FIG. 10 is a schematic side-view illustrating collimated solid viewing angles 202-216 that the periodic structure 164 of the collimator 102 produces when the columns 170-184 of the columns 108 having heights $h_1$-$h_8$ are positioned one by one above the pixels 152 of the pixels 122 of FIGS. 2-4 and 5-7 during a step-by-step lateral scan of the collimator 102 along the arrows 150, respectively. The collimator 102 has eight columns 108 identified as 170-184 having the square openings 104, the septa 106 and heights $h_1$-$h_8$, respectively.

As shown by FIGS. 2-4 and 5-7, when the collimator 102 moves or slides laterally to produce the step-by-step scanning, above the pixel 152 of the pixels 122 the columns 108 having different heights are positioned above the pixels 152 such that for each step the column 108 with different height $h_j$ is positioned above the pixel 152. Above the pixels 152 of FIG. 10, there is a schematic illustration of a virtual column 218. The column 218 is a column similar to the columns 108, but virtually has variable height $h_j$. The height $h_j$ of the column 218 corresponds to the height $h_j$ of one of heights $h_1$-$h_8$ of the columns 170-184 that is positioned above the pixel 152 at the corresponding scan step related to the scan position of the collimator 102. For example, the variable height $h_j$ of the virtual column 218 is $h_1$, $h_2$, $h_3$, $h_4$, $h_5$, $h_6$, $h_7$ or $h_8$ illustrated by the broken lines 186, 188, 190, 192, 194, 196, 198 and 200 corresponding to when the columns 170, 172, 174, 176, 178, 180, 182 and 184 are positioned above the pixel 152, respectively. The collimated solid viewing-angles 202, 204, 206, 208, 210, 212, 214 and 216 are related to the different height $h_1$, $h_2$, $h_3$, $h_4$, $h_5$, $h_6$ $h_7$ and $h_8$ of the columns 170, 172, 174, 176, 178, 180, 182 and 184 of the collimator 102 when positioned above the pixel 152 and correspond to heights 186, 188, 190, 192, 194, 196, 198 and 200 of the virtual variable column 218, respectively.

Figure 11:
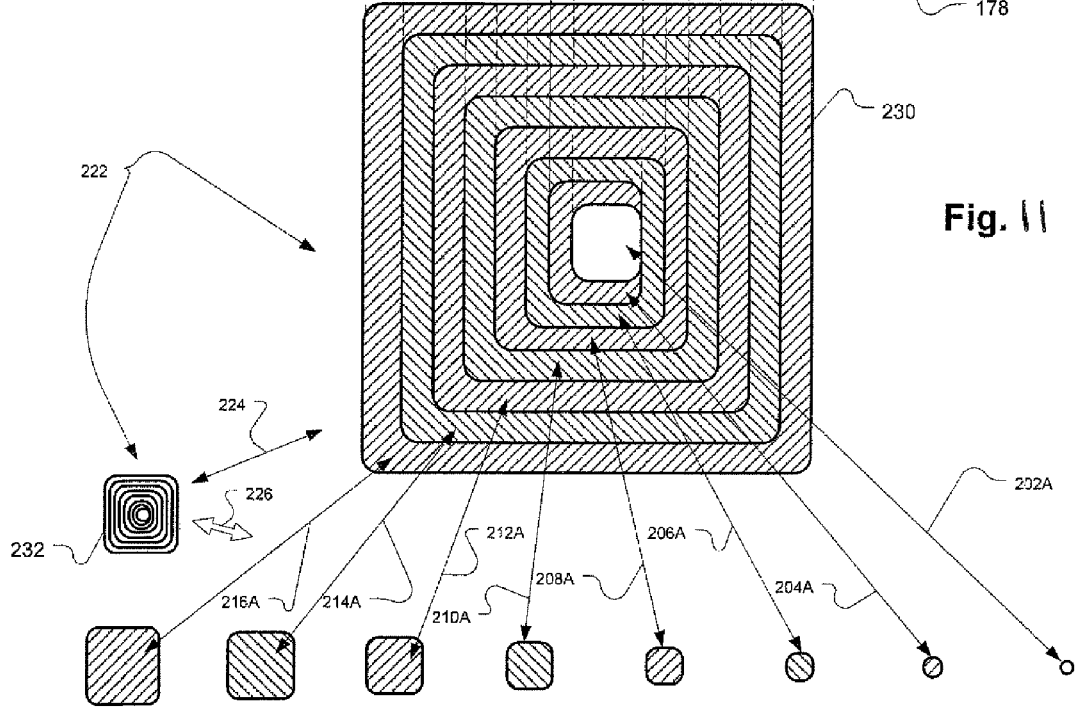
FIG. 11 is a top view illustrating the collimated solid viewing angles of FIG. 10.

FIG. 11 schematically illustrates, by a top view drawing 222, areas 202A, 204A, 206A, 208A, 210A, 212A, 214A and 216A as are observed on a plane 228 by the solid viewing angles 202, 204, 206, 208, 210, 212, 214 and 216 of FIG. 10. The areas observed by the solid angles 202, 204, 206, 208, 210, 212, 214 and 216 on the plane 228 of FIG. 10 are projected, along lines 220, onto FIG. 11 as areas 202A, 204A, 206A, 208A, 210A, 212A, 214A and 216A.

It can be seen that the solid collimated viewing angles 202, 204, 206, 208, 210, 212, 214 and 216 of FIG. 10 and the corresponding areas 202A, 204A, 206A, 208A, 210A, 212A, 214A and 216A on the plane 228 of FIG. 10 as illustrated by FIG. 11, are asymmetric with respect to the central solid angle 202 and the central area 202A of FIG. 11, respectively. This asymmetry is due to the asymmetric structure of the periodic structure 164 that includes the columns 170, 172, 174, 176, 178, 180, 182 and 184 of the collimator 102 in a configuration when each of these columns has a sidewall on the right that is higher than the sidewall on the left. For example, the columns 176 of the structure 164 have a right-hand sidewall having a height $h_5$ and a left-hand sidewall with a height $h_4$ when $h_5 > h_4$.

Group of areas 202A, 204A, 206A, 208A, 210A, 212A, 214A and 216A of FIG. 11 observed by the solid viewing/scanning angles 202, 204, 206, 208, 210, 212, 214 and 216 of FIG. 10 are illustrated in FIG. 11 as the regions 230 and 232. The arrows 224 pointing to the regions 230 and 232 indicate that these regions are the same and are different from each other only by corresponding magnifications. The regions 230 and 232 show the group of areas 202A, 204A, 206A, 208A, 210A, 212A, 214A and 216A as are viewed by the scanning angles 202, 204, 206, 208, 210, 212, 214 and 216 of FIG. 10. The arrows 226 pointing to the region 232 on one hand and on the other hand pointing to the parts that region 232 includes, i.e. areas 202A, 204A, 206A, 208A, 210A, 212A, 214A and 216A, are separated from a corresponding group in the regions 232.

Accordingly, it can be seen that the step-by-step lateral scan of the collimator 102 produces, for pixels 152 (and other pixels 122 of the detector 124 of FIGS. 2-4 and 5-7 as well) different collimations of solid scanning-angles that act as solid scanning angles that produce angular scanning by varying the amount of collimation of the scanning angles. The angular scan of the solid scanning angles 202, 204, 206, 208, 210, 212, 214 and 216 of FIG. 10 creates a 2D scan in the form of a 2D area scan as illustrated by the regions 230 and 232 of FIG. 11. Thus, the lateral step-by-step scan of the collimator 102 produces the 2D angular scan resulting in the 2D area scan for the pixels 122 of the detector 124 of FIGS. 2-4 and 5-7.

For image reconstruction, such as SPECT, the lateral scan of the collimator 102 acquires images by varying the collimation of the scanning angles viewed by the pixels 122 of the detector 124. The pixels 122 collect the radiation emitted from the radiation emitting object, such as the object 134 of FIG. 1. The radiation from the radiation emitting object is received from a surface thereof and a volume via areas thereof, such as the areas 202A, 204A, 206A, 208A, 210A, 212A, 214A and 216A of FIG. 11. The number of images produced, for each pixel 122 during the lateral scan of the collimator 102, is equal to the number N of different collimations that the collimator 102 produces above the pixels 122, such as the pixel 152. The number of collimations for each pixel is equal to the number N of lateral scanning steps of the collimator 102 (N=8 for the example of FIGS. 10 and 11). Accordingly, the number of images C that the detector 124 produces in a scan unit such as the scan unit 100 of FIGS. 2-4, 5-7 and 10 is equal to the number of lateral scanning steps N of the collimator 102 times the number Q of the pixels 122 in the detector 124 as follows:

$$C = N \cdot Q \qquad \text{Eq (1)}$$

For a 3D or SPECT image reconstruction, the number of virtual voxels into which a radiation emitting object, such as the object 134, is divided is equal to the number of images acquired by the scan unit, such as the scan unit 100 of FIGS. 2-4, 5-7 and 10. Each image acquired by each pixel may provide one mathematical equation in which the amount of radiation emitted from each voxel of the radiation emitting object is one unknown. For deriving all the unknowns in the object (the amount of radiation emitted from each voxel in the object) the number of equations should be greater or equal to the number of voxels. The number of equations is equal to the number of data points acquired by all of the pixels 122 of the detector 124 during the lateral scan of the collimator 102. This means that the number of voxels in the radiation emitting object should be equal to C as expressed by Eq (1). This condition ensures that there is a mathematical solution to the set of equations that should be solved for the image reconstruction while preventing the existence of dependent equations. It should be noted that priors (e.g., prior solutions) may be used to reach a convergent solution. Also, it should be noted that with respect to statistical noise, in various embodiments, the solution is a maximum likelihood solution, It can be seen that the lateral scan of the collimator 102 provides the scan unit 100 with a suitable and easy to implement scan process for acquiring and reconstructing 3D and SPECT images in which lateral scanning of the collimator 102 is converted into 2D angular scanning of the solid scanning angles, which in response, creates or results in an area scan of a radiation emitting object.

The scan illustrated by FIGS. 10 and 11 is a progressive scan (e.g., a scan wherein each subsequent step adds new information instead of repeating the acquisition of most of the information) with variable collimation. Accordingly, and as can be seen from FIGS. 10 and 11 in the region 232, which includes the areas 202A, 204A, 206A, 208A, 210A, 212A, 214A and 216A, the larger areas contain all the areas that are smaller than these areas. For example, the area 204A includes the smaller area 202A and the area 216A includes the areas 202A, 204A, 206A, 208A, 210A, 212A and 214A. More generally, each area in the region 232 having a certain reference numeral contains all the areas in the region 232 that with a reference numeral having a value that is smaller than the value of the certain reference numeral. Thus, a large fraction of the images acquired by the scan illustrated by FIGS. 10 and 11 contain the same information that is included in other images as well. This results in repetitive information that does not contribute to the image reconstruction, but increases the statistical noise in a way that may cause poor image reconstruction that may include artifacts. This means that the scan illustrated by FIGS. 10 and 11 is a progressive scan. However, although the scan operation of the scan unit 100 of FIG. 10 is different from other scans, the scan operation may still acquire redundant information.

Accordingly, while the scan operation of FIGS. 10 and 11 demonstrates that the scan unit 100 together with the operational principle thereof is efficient and easy to implement, the scan unit 100 may still acquire redundant information for forward looking variable collimation.

Figure 12:
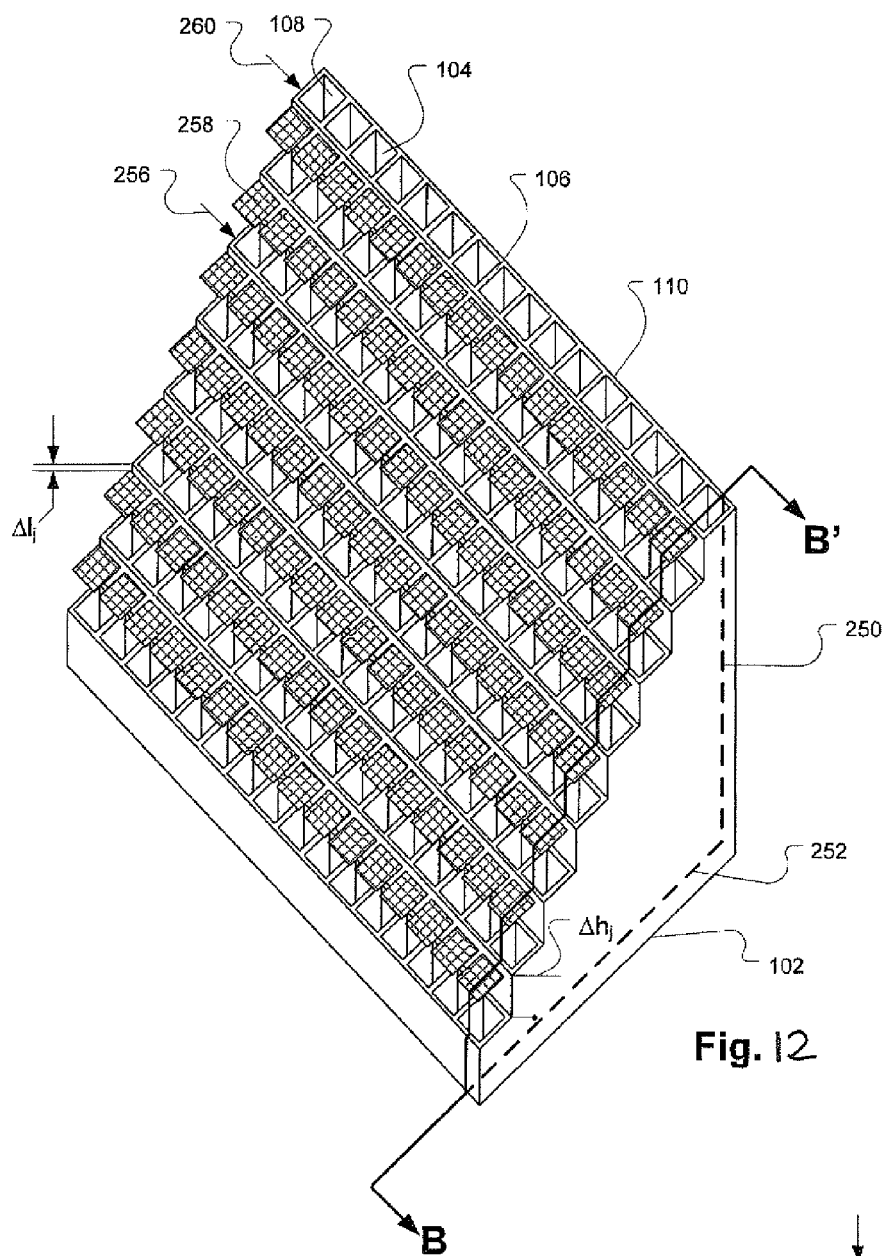
FIG. 12 is a schematic perspective view of a portion of a collimator illustrating a periodic structure in accordance with another embodiment.
Figure 13:
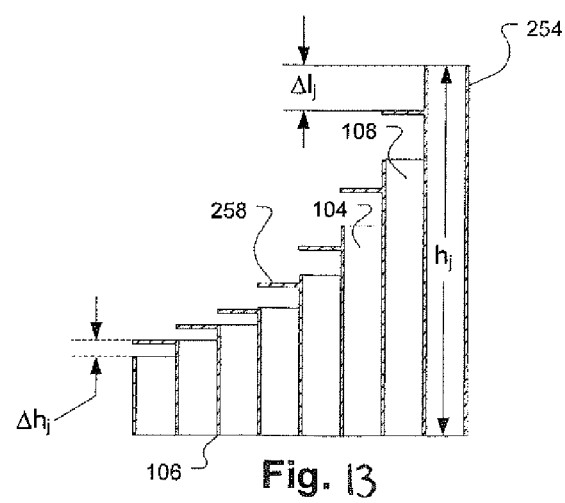
FIG. 13 is a side view cross-section B-B' of the collimator of FIG. 12.

To reduce or avoid generating repetitive or redundant information acquired during the scan of the collimator 102, screenings 258 (or screens) such as illustrated by FIGS. 12 and 13 are attached to the columns 108 to avoid forward looking scanning solid angles of the collimator 102. The screenings 258 allow only tilted scanning angles such that each tilted scanning angle produced by one of the groups of columns 108 in the periodic structure 110 is different from the tilted scanning angles of other groups in the collimator 102 and observes substantially different regions on and in the radiation emitting object. Accordingly, each image collected during the scan of the collimator 102, by the pixels 122 of the radiation detector 124 of FIGS. 2-4 and 5-7, via the collimator 102 to which the screenings 258 were added as shown in FIGS. 12 and 13 is substantially different from the other images acquired during the scan of the collimator 102. Thus, the repetitive information is eliminated. FIGS. 12 and 13 illustrate the perspective and cross-section views of the collimator 102, respectively, which includes the periodic structure 110 that contains the screenings 258. The solid scanning angles produced during the scan by the collimator 102 of FIGS. 12 and 13 having the screenings 258 are shown in FIGS. 14 and 15.

FIG. 12 is a schematic perspective view of part of the collimator 102 showing one periodic structure 110 of the collimator 102. The collimator 102 includes eight groups of columns 108 arranged along rows 256 of the periodic structure 110 in the illustrated embodiment. Each group of columns 108 has a different height $h_j$ and two adjacent groups are different in height by an amount $\Delta h_j$. The columns 108 have square openings 104 and are separated by the septa 106. The Stepped line B-B' and the lines 250 and 252 define a cross-section plane along which the periodic structure 110 may be cut to form a side-view cross-section similar to the side-view cross-section illustrated by FIG. 9. The radiation screenings 258 having length $Z_j$ are placed above the openings 104 and configured to block the radiation impinging on surfaces thereof to allow only inclined scanning viewing angles via the openings 104 to ensure, in various embodiments, that there is no forward looking scanning, which results in the repetitive information of the scan unit, such as the scan units 100 of FIGS. 2-4, 5-7 and 10-11. The group of columns 108 arranged along the arrow 260 of the arrows 256 may not have the screenings 258 since the collimation of the columns 108 is the narrowest collimation in the collimator 102. In such a case, the viewing angles of the columns 108 in the group 260 cannot include any other viewing angles of other groups (rows in the collimator 102) and thus cannot contain repetitive information even in a configuration of forward looking scanning.

FIG. 13 is a side-view cross-section 254 of the periodic structure similar to the periodic structure 110 of FIG. 12. The side-view cross-section 254 may not be proportional to the cross-section of the structure 110 of FIG. 12 that is cut along plane A-A'. To illustrate that the height differences $\Delta h_j$ can be selected as desired, FIG. 13 shows the height differences $\Delta h_j$ between the columns 108 as being different from the height differences $\Delta h_j$ between the columns 108 of FIG. 12. Similarly, to illustrate that the height differences between the screenings 258 and the top edges of the columns 108 to which the screenings 258 are attached can be selected as desired, FIG. 12 illustrates the height differences $\Delta l_j$ as being different from the height differences $\Delta h_j$ as illustrated by FIG. 13. Even though the screenings 258 are illustrated by FIG. 13 as having the same length $Z_j$ for all the groups of columns 108, it should be understood that each group of columns 108 may have a different length $Z_j$ of screening 258.

Figure 14:
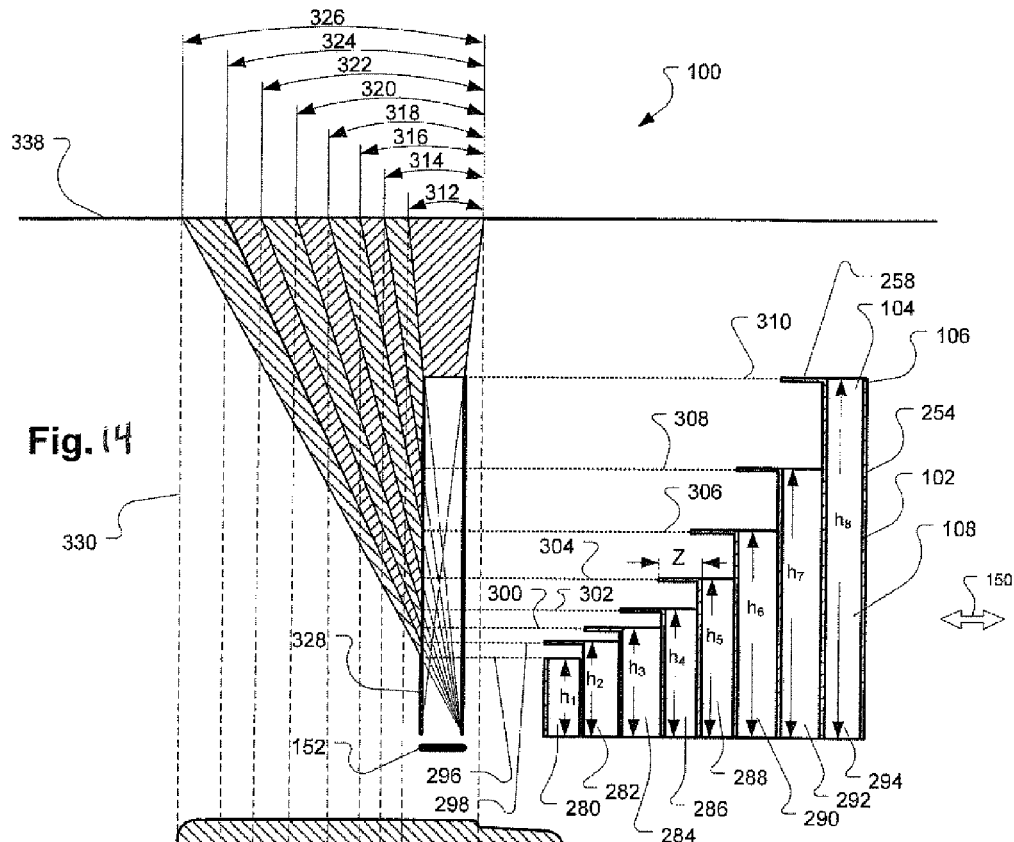
FIG. 14 is a schematic side view illustrating collimated solid viewing angles in accordance with another embodiment.
Figure 15:
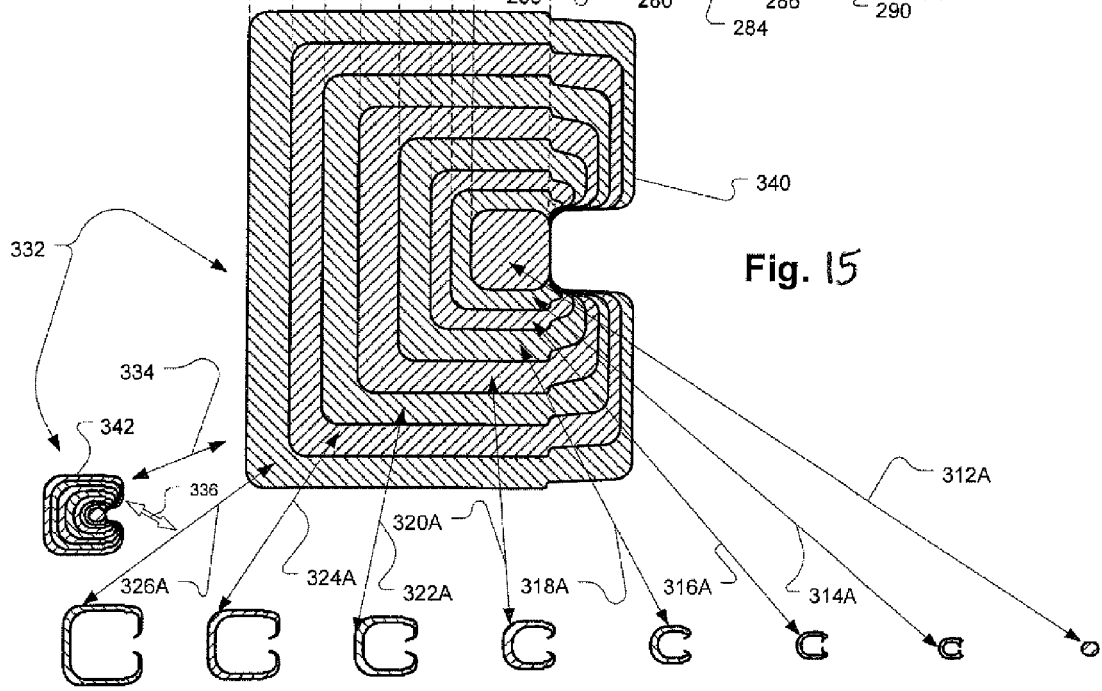
FIG. 15 is a top view illustrating the collimated solid viewing angles of FIG. 14.

FIG. 14 is a schematic side-view illustrating the collimated solid viewing angles 312-326 that the part 254 of the periodic structure of collimator 102 produces when the columns 280-294 of the columns 108 having heights $h_1$-$h_8$ are positioned one by one above the pixels 152 of the pixels 122 of FIGS. 2-4 and 5-7 during a step-by-step lateral scan of the collimator 102 along the arrows 150, respectively. The collimator 102 has eight columns 108 in the illustrated embodiment identified as 280-294 having the square openings 104, the septa 106 and heights $h_1$-$h_8$, respectively. The part of the columns 108 have the radiation screenings 258 attached thereto and having length $Z_j$ that may have a different value for each index j corresponding to different height $h_j$.

As shown by FIGS. 2-4 and 5-7, when the collimator 102 moves or slides laterally to produce the step-by-step scanning, above the pixel 152 of the pixels 122, the columns 108 having different heights are positioned above the pixels 152 such that for each step, the column 108 with different height $h_j$ is positioned above the pixel 152. Above the pixels 152 of FIG. 14 there is a schematic illustration of a virtual column 328. The column 328 is similar to the columns 108, but virtually has variable height $h_j$. The height $h_j$ of the column 328 corresponds to the height $h_j$ of one of the heights $h_1$-$h_8$ of the columns 280-294 that is positioned above the pixel 152 at the corresponding scan step related to the scan position of the collimator 102. For example, the variable height $h_j$ of the virtual column 328 is $h_1$, $h_2$, $h_3$, $h_4$, $h_5$, $h_6$, $h_7$ or $h_8$ illustrated by the broken lines 296, 298, 300, 302, 304, 306, 308 and 310 corresponding to when the columns 280, 282, 284, 286, 288, 290, 292 and 294 are positioned above the pixel 152, respectively.

The collimated solid viewing-angles 312, 314, 316, 318, 320, 322, 324 and 326 correspond to the different heights $h_1$, $h_2$, $h_3$, $h_4$, $h_5$, $h_6$, $h_7$ and $h_8$ of the columns 280, 282, 284, 286, 288, 290, 292 and 294 of the collimator 102 when positioned above the pixel 152 and correspond to the heights 296, 298, 300, 302, 304, 306, 308 and 310 of the virtual variable column 328, respectively.

FIG. 15 schematically illustrates, by a top view drawing 332, the areas 312A, 314A, 316A, 318A, 320A, 322A, 324A and 326A as are observed on the plane 338 by the solid viewing angles 312, 314, 316, 318, 320, 322, 324 and 326 of FIG. 14. The areas observed by the solid angles 312, 314, 316, 318, 320, 322, 324 and 326 on the plane 338 of FIG. 14 are projected, along the lines 330, onto FIG. 15 as the areas 312A, 314A, 316A, 318A, 320A, 322A, 324A and 326A.

It can be seen that the solid collimated viewing angles 312, 314, 316, 318, 320, 322, 324 and 326 of FIG. 14 and the areas 312A, 314A, 316A, 318A, 320A, 322A, 324A and 326A observed on the plane 338 of FIG. 14 as are illustrated by FIG. 15, are asymmetric with respect to the central solid angle 312 and the central area 312A of FIG. 15, respectively. This asymmetry is due to the asymmetric structure of the periodic structure 254 that includes the columns 280, 282, 284, 286, 288, 290, 292 and 294 of the collimator 102 in a configuration when each of these columns has a sidewall on the right that is higher than the sidewall on the left. For example, the columns 292 of the structure 254 have a right-hand sidewall having a height close to $h_8$ and a left-hand sidewall with a height close to $h_7$ where $h_8 > h_7$.

The above described asymmetry is mainly due to the screenings 258 that allow the inclined scanning angles oriented toward the openings underneath the screenings 258. This creates the inclined scanning angles 312, 314, 316, 318, 320, 322, 324 and 326 that are oriented and scan only to the left. The only scan angle that is symmetric relative to the center of the virtual column 328 is the scanning angle 312 having the narrower collimation, which is related to the group 260 of the columns 108 of FIG. 12. The group 260 may not include the screenings 258 and may have forward looking scanning angle since the group 260 cannot produce repetitive scan information as being the narrowest scan angle that cannot contain other scanning angles.

The group of areas 312A, 314A, 316A, 318A, 320A, 322A, 324A and 326A of FIG. 15 observed by the solid viewing/scanning angles 312, 314, 316, 318, 320, 322, 324 and 326 of FIG. 14 are illustrated by FIG. 15 as the regions 340 and 342. The arrows 334 pointing to the regions 340 and 342 indicate that these regions are the same and are different from each other only by corresponding magnifications. The regions 340 and 342 show the group of areas 312A, 314A, 316A, 318A, 320A, 322A, 324A and 326A as are viewed by the scanning angles 312, 314, 316, 318, 320, 322, 324 and 326 of FIG. 14. The arrows 336 pointing to the region 342 on one hand and on the other hand pointing to the parts that the region 342 includes, i.e. the areas 312A, 314A, 316A, 318A, 320A, 322A, 324A and 326A, which are separated from each other and from the corresponding group in the region 342.

Accordingly, it can be seen that the step-by-step lateral scan of the collimator 102 produces, for the pixels 152 (and other the pixels 122 of the detector 124 of FIGS. 2-4 and 5-7 as well) different collimations of solid scanning-angles that act as solid scanning angles that produce angular scanning by varying the amount of collimation of the scanning angles. The angular scan of the solid scanning angles 312, 314, 316, 318, 320, 322, 324 and 326 of FIG. 14 creates a 2D scan in the form of a 2D area scan as illustrated by the regions 340 and 342 of FIG. 15. Thus, the lateral step-by-step scan of the collimator 102 produces the 2D angular scan that produces the 2D area scan for the pixels 122 of the detector 124 of FIGS. 2-4 and 5-7.

For image reconstruction, such as SPECT, the lateral scan of the collimator 102 acquires images by varying the collimation of the scanning angles viewed by the pixels 122 of the detector 124. The pixels 122 collect the radiation emitted from the radiation emitting object, such as the object 134 of FIG. 1. The radiation from the radiation emitting object is received from a surface thereof and a volume via areas thereof, such as the areas 312A, 314A, 316A, 318A, 320A, 322A, 324A and 326A of FIG. 15. The number of images produced, for each pixel 122 during the lateral scan of the collimator 102, is equal to the number N of different collimations that the collimator 102 produces above the pixels 122, such as the pixel 152. The number of collimations for each pixel is equal to the number N of lateral scanning steps of collimator 102 (N=8 for the example of FIGS. 14 and 15). Accordingly, as described for FIGS. 10 and 11, the number of images C that the detector 124 produces in a scan unit such as the scan unit 100 of FIGS. 2-4, 5-7 and 14 is equal to the number of lateral scanning steps N of the collimator 102 times the number Q of the pixels 122 in the detector 124 as in Eq (1).

It can be seen that the lateral scan of the collimator 102 provides the scan unit 100 with a suitable and easy to implement scan operation for acquiring and reconstructing 3D and SPECT images in which lateral scanning of the collimator 102 is converted into the 2D angular scanning of the solid scanning angles, which in response creates the area scan of a radiation emitting object.

Except for the group 260 of the columns 108 shown in FIG. 12, the scan illustrated by FIGS. 14 and 15 is a non-forward looking scan with variable collimation. In addition, unlike the arrangements illustrated by FIGS. 10 and 11, the heights $h_1$, $h_2$, $h_3$, $l_4$, $h_5$, $h_6$ $h_7$ and $h_8$ of the columns 108 and the positions of the screenings 258 corresponding to these heights are adjusted to produce the scanning tilted angles 314, 316, 318, 320, 322, 324 and 326 that do not contain each other and do not overlap each other. Accordingly, and as can be seen from FIGS. 14 and 15, in the regions 340 and 342, which include the areas 312A, 314A, 316A, 318A, 320A, 322A, 324A and 326A, no area of the areas 312A, 314A, 316A, 318A, 320A, 322A, 324A and 326A contain or overlap other areas from the region 342. The arrows 336 pointing to the region 342 on one hand and on the other hand pointing to the parts that the region 342 includes, i.e. areas 312A, 314A, 316A, 318A, 320A, 322A, 324A and 326A, are separated from each other and from a corresponding group in regions 342 such that none of the areas in regions 340 and 342 contains or overlaps other areas in these regions.

The scan system 100 of FIGS. 14 and 15 produces images, for each scan/step position of the collimator 102, in a way that each image acquired by the scan of unit 100 is substantially different from other images acquired by the scan of the system 100 of FIGS. 14 and 15 to produce radiation scanning without redundancy and repetitive information. Unlike the arrangements illustrated by FIGS. 10 and 11 in which the scan of unit 100 causes repetitive information, the scan unit 100 of FIGS. 14 and 15 does not produce repetitive information and all the information acquired by the scan system 100 of FIGS. 14 and 15 contributes to the image reconstruction. This is achieved as a result of the scan illustrated by FIGS. 14 and 15 being a non-forward looking scan. Accordingly, the scan operation of FIGS. 14 and 15 illustrates the scan unit 100 that is efficient, easy to implement and at the same time provides information acquired during the scan, which substantially does not include redundant and repetitive information. In various embodiments, this allows reconstructing high quality 3D or SPECT images in an efficient way with reduced artifacts.

From FIGS. 14 and 15 and the corresponding description above it should be understood that adding the screenings 258 to the collimator 102 in an appropriate design may avoid generating repetitive information acquired during the scan of the collimator 102 as illustrated by FIGS. 10 and 11. The design of the screenings 258 is based on the selection of the following:

1. the heights $h_1$, $h_2$, $h_3$, $h_4$, $h_5$, $h_6$ $h_7$ and $h_8$ of the columns 108 in the groups 256;
2. the spaces $\Delta l_j$ (see FIG. 13) between the screenings 258 and the edges of the columns 108 to which the screenings 258 are attached;
3. the height differences $\Delta h_j$ between the columns 108 of the groups 256; and
4. the length $Z_j$ of the screenings 258.

The proper selection of the above listed parameters ensures that the scanning tilted angles 314, 316, 318, 320, 322, 324 and 326 do not contain each other and do not overlap each other. Thus, the scanning angles 312A, 314A, 316A, 318A, 320A, 322A, 324A and 326A do not contain each other and do not overlap each other as well as produce a radiation scan with no redundancy and repetitive information.

Figure 16:
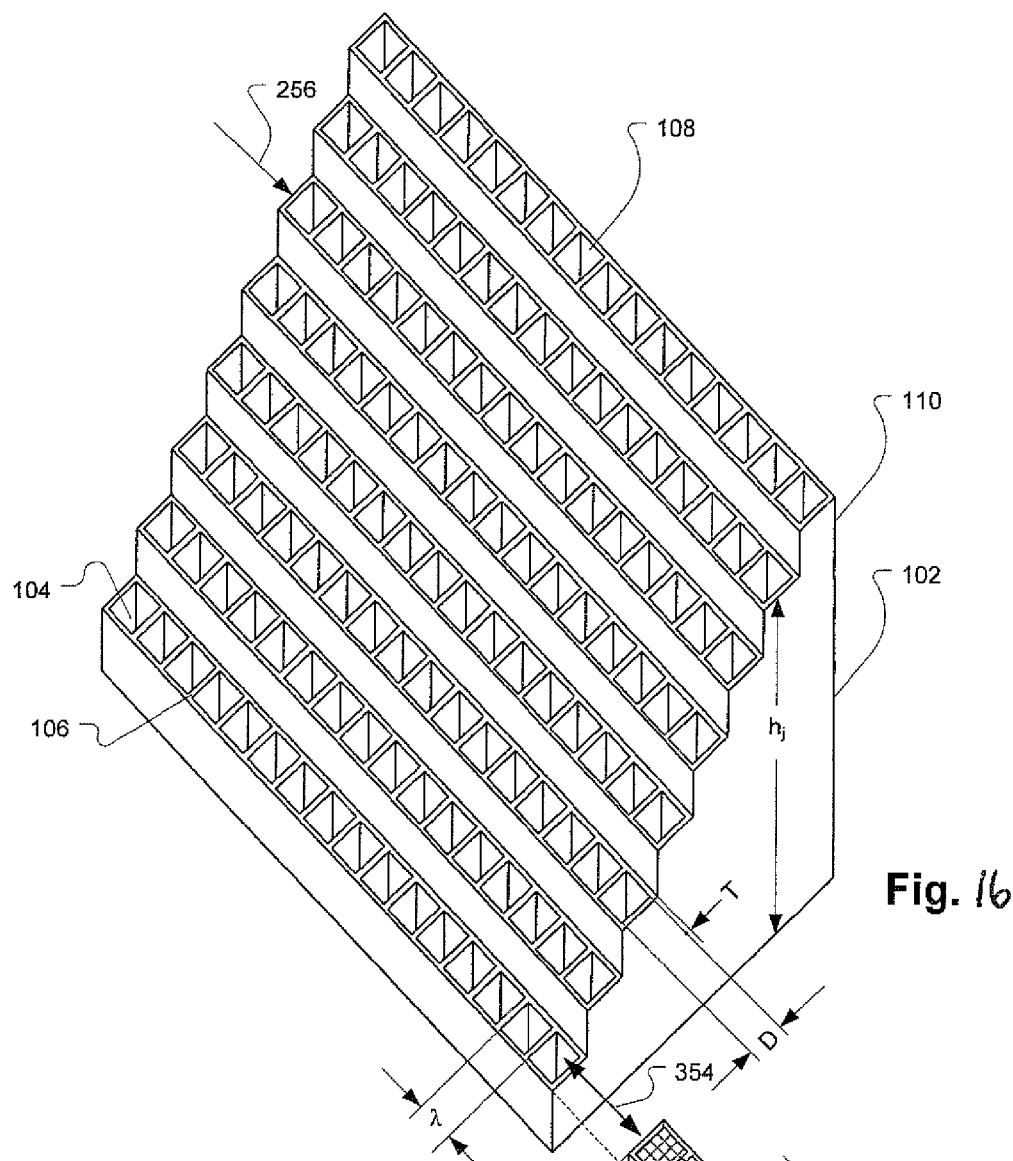
FIG. 16 is a schematic perspective view of a portion of a periodic structure of a collimator in accordance with an embodiment.
Figure 17:
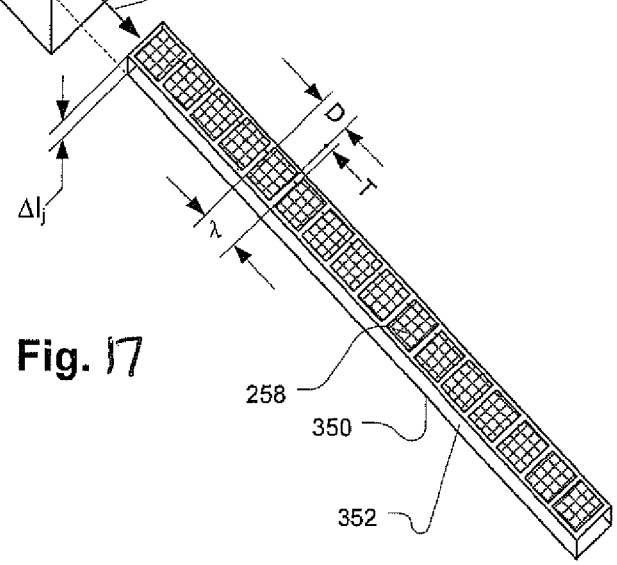
FIG. 17 is a schematic perspective illustration of a substrate carrier in accordance with an embodiment.

FIGS. 16 and 17 schematically illustrate the screenings 258 attached to the collimator 102 to construct the configuration 254 of the collimator 102 as illustrated by FIG. 14. FIG. 16 is a schematic perspective illustration of the structure 110, which is a part of the periodic structure of the collimator 102 having the columns 108 arranged in eight groups according to heights $h_j$ and along the row 256. The columns 108 have the openings 104 with size D and are separated by the septa 106 having thickness T. The 2D pitch $\lambda$ of the collimator 102 is equal to the sum of the size D of the opening 104 and the thickness T of the septum 106.

FIG. 17 is a schematic perspective illustration of a substrate carrier 350 made of material that is substantially transparent to the ionizing radiation emitted from the radiation emitting object, such as the object 134 of FIG. 1, which is used for the imaging. The screenings 258 are placed on the carrier 350 having a shape of a bar 352 in one embodiment. The screenings 258 may be attached to the bar 352 using, for example, a suitable material such as glue, or pressed into the bar 352 to be indented therein. The screenings 258 are arranged on the bar 352 in a linear array form having a pitch $\lambda$ which is the same as the 2D pitch of the collimator 102 of FIG. 16. The sizes $Z_j$ of the screenings 258 and the space between the screenings 258 are similar to the size D of the openings 104 and the thickness T of the septa 106 of FIG. 16, respectively.

The arrows 354 show that the carrier 350 with the screenings 258 on top thereof are placed above the columns 108 of the collimator 102 of FIG. 16 in the direction of the groups of columns 108 along the rows 256. The bar 352 is attached to the collimator 102 along the rows 256 using, for example, glue that is transparent to the ionized radiation used. The bar 352 is placed and glued to the collimator 102 when the centers of the screenings 258 are aligned with the centers of openings 104 of the columns 108 of the collimator 102 of FIG. 16. Bars like the bar 352 may be placed above all of the openings 104 of the collimator 102 or only above part of the openings 104.

When the bar 352 is positioned above the openings 104, the height $\Delta h_j$-$\Delta l_j$ (see FIG. 12) of the screenings 258 above the openings 104 is equal to the thickness of the bar 352. This thickness may be selected as desired to adjust the height $\Delta l_j$ of the screenings 258 above the openings 104. The height $\Delta h_j$-$\Delta l_j$ may be different for each group of columns 108. In this case, each bar, such as the bar 352 placed along the rows 256 would have different thickness corresponding to the desired heights $\Delta h_j$-$\Delta l_j$.

Figure 18:
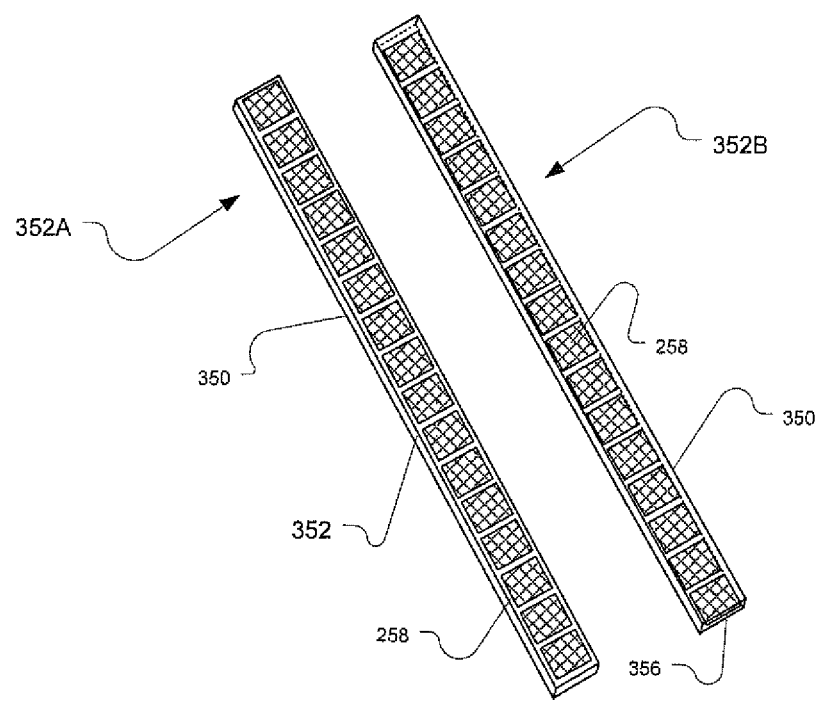
FIG. 18 illustrates perspective views of the substrate carrier of FIG. 17.

FIG. 18 shows the bar 352 of FIG. 17 in two schematic perspective views to better illustrate the structure of the bar 352. The bar 352 of FIG. 17 is shown in FIG. 18 in two views 352A and 352B. In the view 352B, the screenings 258 are facing up similar to that illustrated by FIG. 17 where the bar 352 is placed on the collimator 102 along the row 256 when the screenings 258 are facing up and placed on top of the radiation-transparent substrate 350. Similarly, in the view 350A, the screenings 258 are facing down when the radiation transparent material is placed on top of the screenings 258. The screenings 258 may be, for example, glued to the substrate 350 or pressed to be indented in the substrate 350 as can be seen at the sidewall of the substrate 350 in the view 352B where the screening 258 is pressed into the cavity 356 in the substrate 350. The screenings 258 are made from radiation-blocking materials, such as lead (Pb) or tungsten (W) and have thicknesses ensuring that most of the ionizing radiation used for the imaging is absorbed in the screenings 258.

Figure 19:
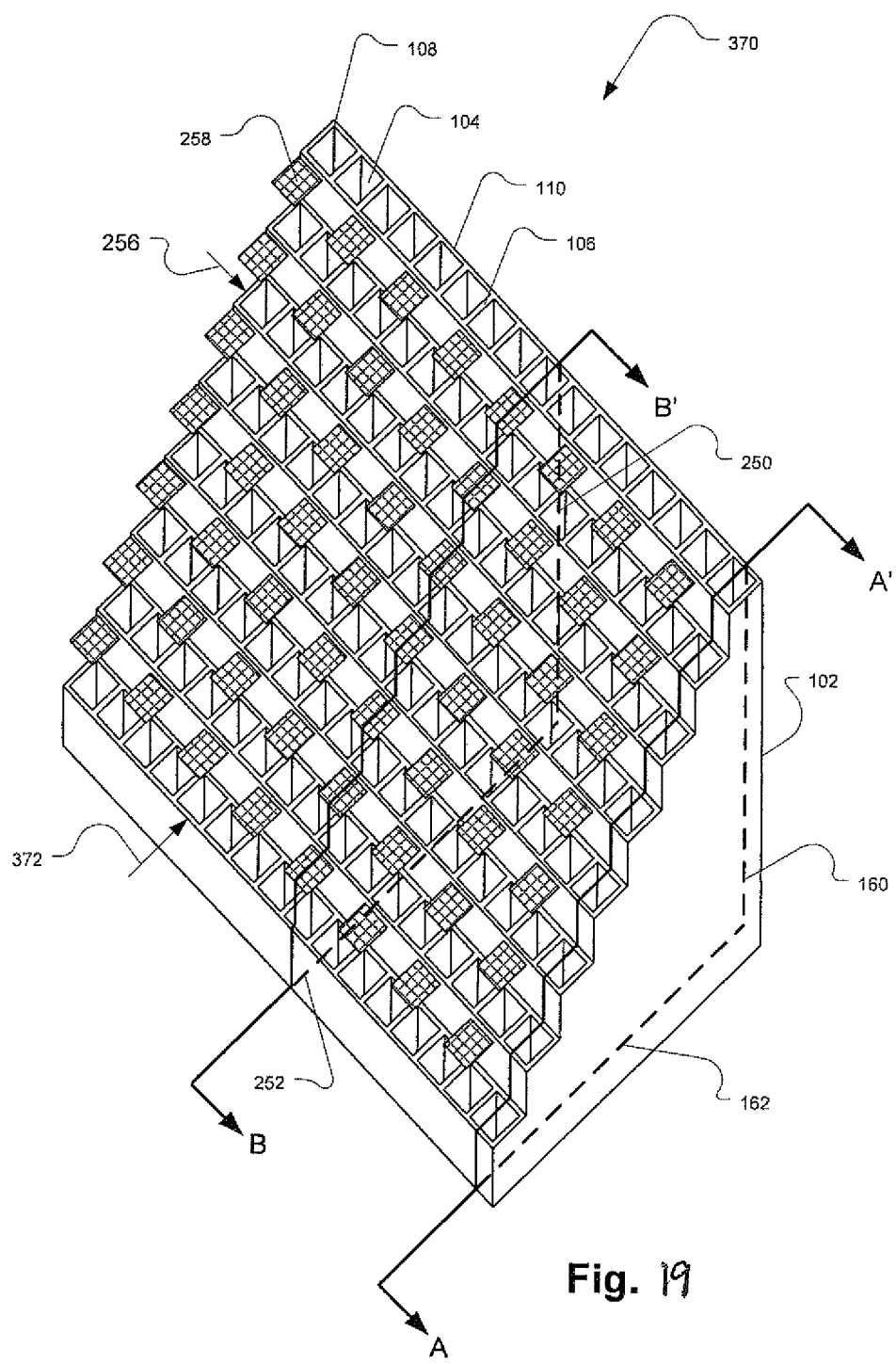
FIG. 19 is a schematic perspective illustration of a portion of a periodic structure of a collimator in accordance with another embodiment.

FIG. 19 is a schematic perspective illustration 370 of a part 110 of the periodic structure of the collimator 102 having the columns 108 arranged in eight groups along the rows 256 according to height. The columns 108 have the openings 104 and the septa 106. The screenings 258 are placed above the openings 104 using the substrate carriers similar to the carriers 350 of FIGS. 17 and 18. The illustration 370 of FIG. 19 is similar to that illustrated by FIG. 12 except that the screenings 258 are placed above every second line of the lines 372 of the collimator 102 to form spaces, which are not occupied by the screenings 258, between the lines 372 along which the screenings 258 are arranged. The spaces without screenings 258 between the lines 372 along which the screenings 258 are arranged allow the screenings 258 to have lateral dimensions larger than the size D of the openings 104 or even larger than the 2D pitch λ of the collimator 102.

The large screenings 258 may be configured to improve the discrimination between the solid scanning angles such as the scanning tilted angles 312, 314, 316, 318, 320, 322, 324 and 326 of FIG. 14 that substantially do not contain each other and do not overlap each other for enabling high quality image reconstruction. On the other hand, the lines 372 of the columns 108 that do not have the screenings 258 there above operate like a forward-looking collimator with variable collimation. Thus, the lines 372 of the columns 108 produce scanning angles that contain each other and overlap each other in a way that may produce repetitive information during the scan, but with very high sensitivity.

The regions in the collimator 102 having the large screenings 258 provide radiation-scanning that allows a very high-quality image reconstruction. On the other hand, the regions in the collimator 102 that have no screenings 258 above the collimator 102 provide radiation-scanning that allows scanning with very high sensitivity.

The cross-section plane defined by stepped line A-A' and the lines 160 and 162 is oriented along the line 372 of the columns 108 having no screenings 258 above the columns 108. This cross-section plane is similar to the cross-section plane defined by the stepped line A-A' and the lines 160 and 162 of FIG. 8, which corresponds to the side-view cross-section illustrated by FIG. 9. Similarly, the cross-section plane defined by the stepped line B-B' and the lines 250 and 252 is oriented along a line of the columns 108 having the large screenings 258 there above. This cross-section plane is similar to the cross-section plane defined by the stepped line B-B' and the lines 250 and 252 of FIG. 12 corresponding to the side-view cross-section illustrated by FIG. 13.

The structure 370 of FIG. 19 that combines scanning solid angles of the type that do not contain each other and do not overlap each other with the type that contain each other and overlap each other may provide a good compromise between ultra-high sensitivity of the collimator 102 and the very high image quality that the collimator 102 provides.

Figures 20, 21:
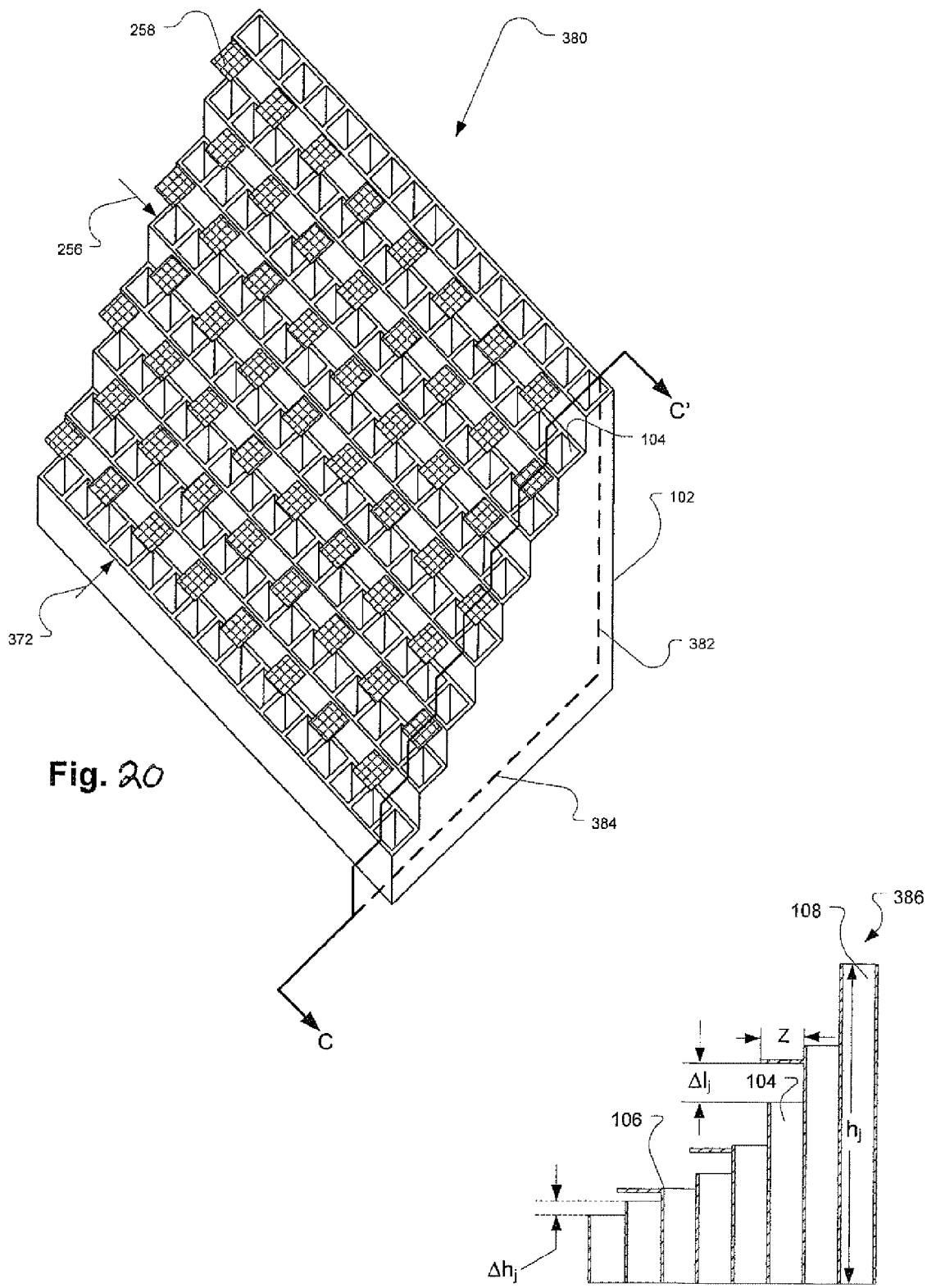
FIG. 20 is a schematic perspective view of a portion of a collimator illustrating a periodic structure in accordance with another embodiment.
FIG. 21 is a side view cross-section C-C' of the periodic structure of FIG. 20.

FIG. 20 is a schematic perspective view 380 of part of the collimator 102 showing one periodic structure 110 of the collimator 102. The collimator 102 includes eight groups of columns 108 arranged along the rows 256 of the part 110. Each group of columns 108 has a different height $h_j$ and two adjacent groups are different in height by an amount $\Delta h_j$. In this embodiment, the columns 108 have square openings 104 and are separated by the septa 106. The stepped line C-C' and the lines 382 and 384 define a cross-section plane along which the part 110 may be cut to form a side-view cross-section similar to the side-view cross-section illustrated by FIGS. 9 and 13. The radiation screenings 258 having length $Z_j$ are placed above the openings 104 and configured to block the radiation impinging on surfaces thereof to allow only inclined scanning viewing angles passing via the openings 104 to ensure, in various embodiments, that there is no forward looking scanning which results in repetitive information of the scan unit, such as the scan units 100 of FIGS. 2-4 and 5-7.

The group of columns 108 arranged along the arrow 260 of the arrows 256 may not have the screenings 258 since the collimation of the columns 108 is the narrowest collimation in the collimator 102. In such a case, the viewing angles of the columns 108 in the group 260 cannot include any other viewing angles of other groups (rows in the collimator 102) and thus cannot contain repetitive information even in a configuration of forward looking scanning.

As described above, the screenings 258 having lateral dimension $Z_j$ larger than the pitch λ of the collimator 102 may improve the quality of the reconstructed image. FIG. 20 illustrates the configuration 380 in which the screenings 258 having the dimension $Z_j$ larger than the pitch size λ can be arranged along every other line 256 of the collimator 102. FIG. 20 illustrates the structure 380 which is an alternative structure to the structure 370 of FIG. 19 in which the screenings 258 having the dimension $Z_j$ larger than the pitch size λ of the collimator 102 can be arranged, but in an alternative configuration. According to the configuration 380, the screenings 258 are arranged above the columns 108 in a way that each column 108 having the screening 258 there above, is surrounded by four columns 108 having no screenings 258 there above to form a structure in which the screenings 258 appear, from a top view of the structure 380 as being arranged in a pattern similar to the pattern of a chess-board or checkerboard.

FIG. 21 is a side-view cross-section 386 of a part similar to the part 110 of FIG. 20. The side-view cross-section 386 may not be proportional to the cross-section of the structure 110 of FIG. 20 that is cut along plane C-C'. To illustrate that the height differences $\Delta h_j$ can be selected as desired, FIG. 21 shows the height differences $\Delta h_j$ between the columns 108 as being different from the height differences $\Delta h_j$ between the columns 108 of FIG. 20. Similarly, to demonstrate that the height differences between the screenings 258 and the top edges of the columns 108 to which the screenings 258 are attached can be selected as desired, FIG. 21 illustrates heights, $h_j$ and height differences $\Delta h_j$ and $\Delta l_j$ as being different for some of the columns 108. The lateral size of the screenings 258 may be selected as desired and can be chosen to be larger than the size D of the opening 104 or can be larger than the size of the 2D pitch λ of the collimator 102.

Figures 22, 23:
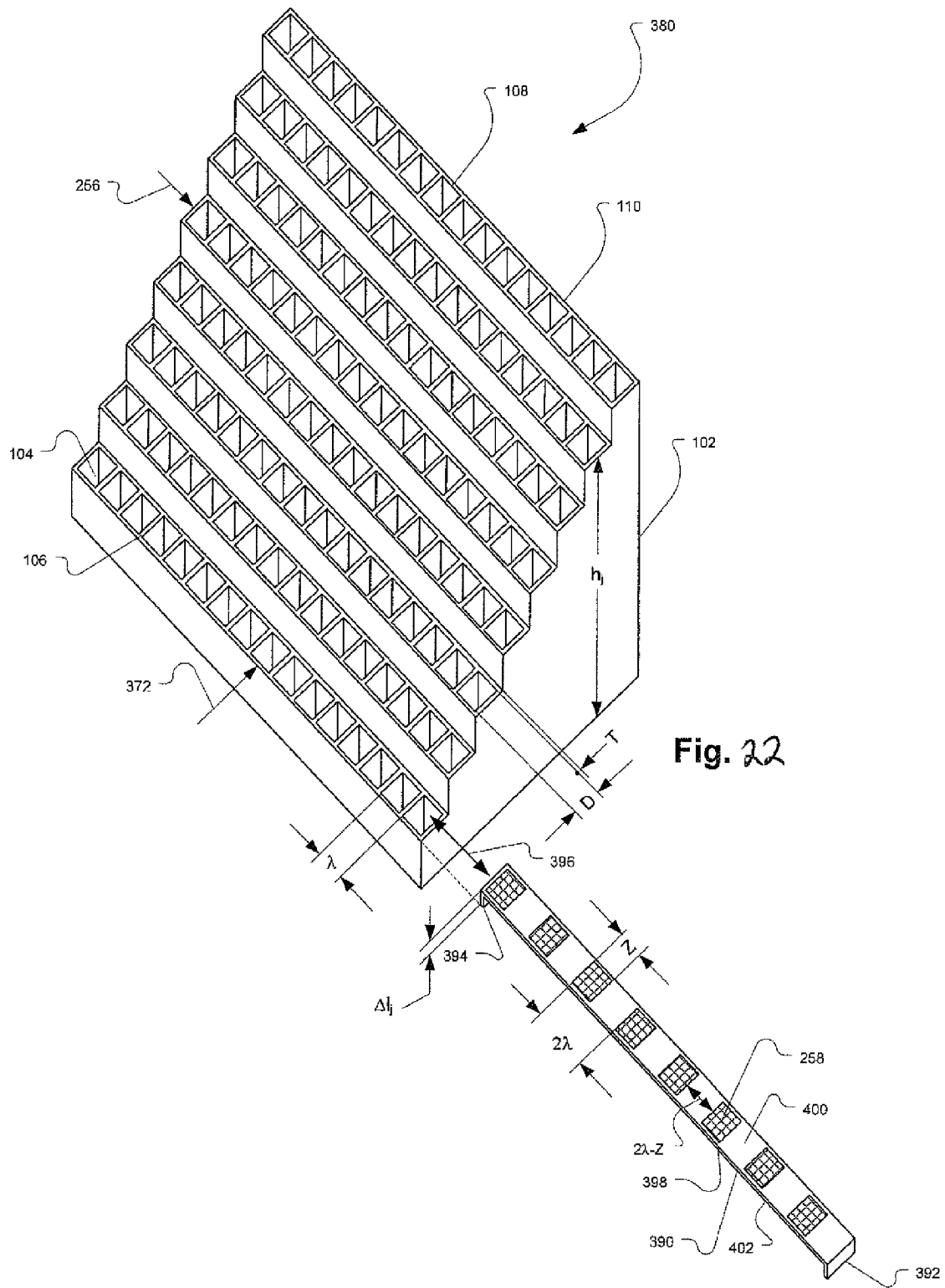
FIG. 22 is a schematic perspective view of a portion of a periodic structure of a collimator with screenings that may be attached in accordance with another embodiment.
FIG. 23 is a schematic perspective illustration of a substrate carrier in accordance with another embodiment that may be attached to the collimator of FIG. 22.

FIGS. 22 and 23 schematically illustrate the screenings 258 attached to the collimator 102 to construct a configuration 380 of the collimator 102 as illustrated by FIG. 22. FIG. 22 is a schematic perspective illustration of the periodic structure 110 which is part of the collimator 102 having the columns 108 arranged in eight groups according to heights $h_j$ and along the row 256. The heights of the groups of columns 108 which are arranged along the rows 256 are varied along the lines 372. The columns 108 have the openings 104 with the size D and are separated by the septa 106 having a thickness T. The 2D pitch λ of the collimator 102 is equal to the sum of the size D of opening 104 and the thickness T of the septum 106.

FIG. 23 is a schematic perspective illustration of the substrate carrier 390 made of or formed from a material that is substantially transparent to the ionizing radiation emitted from the radiation emitting object, such as the object 134 of FIG. 1, which is used for the imaging. The screenings 258 are placed on the carrier 390 having the shape of the bar 398 having an upper surface 400 and a lower surface 402. The legs 392 and 394 of the substrate 390 support the bar 398. The screenings 258 may be attached to the bar 398, on the upper surface 400 using, for example, glue or being pressed into the bar 398 to be indented therein. In one embodiment, the screenings 258 are arranged on the surface 400 of the bar 398 in a linear array form having a pitch equal to 2λ, which is twice the 2D pitch λ of the collimator 102 of FIG. 22. The size $Z_j$ of the screenings 258 is larger than the pitch λ of the collimator 102 and the space between adjacent screenings 258 is 2λ-Z.

The arrows 396 illustrate that the carrier 390 with the screenings 258 on top thereof are placed above the columns 108 of the collimator 102 of FIG. 22 in the direction of the groups of columns 108 along the rows 256. The bar 398 is supported by the legs 392 and 394 which are attached to the collimator 102 along the rows 256 using, for example, glue that is transparent to the ionizing radiation used. The legs 392 and 394 are placed and glued to the collimator 102 when the centers of the screenings 258 are aligned with the centers of the openings 104 of the columns 108 of the collimator 102 of FIG. 22. Bars like the bar 398 may be placed above all the openings 104 of the collimator 102 or only above part of the openings 104.

When the bar 398 is positioned in place above the openings 104, the height $\Delta h_j$-$\Delta l_j$ of the screenings 258 above the openings 104 is equal to the heights of the legs 392 and 394 as measured from surface the 400. These lengths may be selected as desired to adjust the height $\Delta h_j$-$\Delta l_j$ of the screenings 258 above the openings 104. The height $\Delta h_j$-$\Delta l_j$ may be different for each group of columns 108. In this case, each bar, such the bar 398 placed along rows 256 would have different legs 392 and 394 corresponding to the desired heights $\Delta h_j$-$\Delta l_j$.

The bar 398 of the substrate 390 of FIG. 23 is different from the bar 352 of the substrate 350 of FIG. 17 in thickness. When producing the same height different $\Delta h_{ia}$-$\Delta l_j$ of the screenings 258 above the openings 104 using the bars 398 and 352, the thickness of the bar 398 is less than the thickness of the bar 352 due to the use of the legs 392 and 394 in the substrate 390 of FIG. 23. While the bars 398 and 352 of FIGS. 23 and 17, respectively, are both transparent to the ionizing radiation used for the imaging, the reduced thickness of the bar 398 ensures that the amount of radiation scatter in the bar 398 is less than the radiation scatter in the bar 352 which is thicker than the bar 398.

Figure 24:
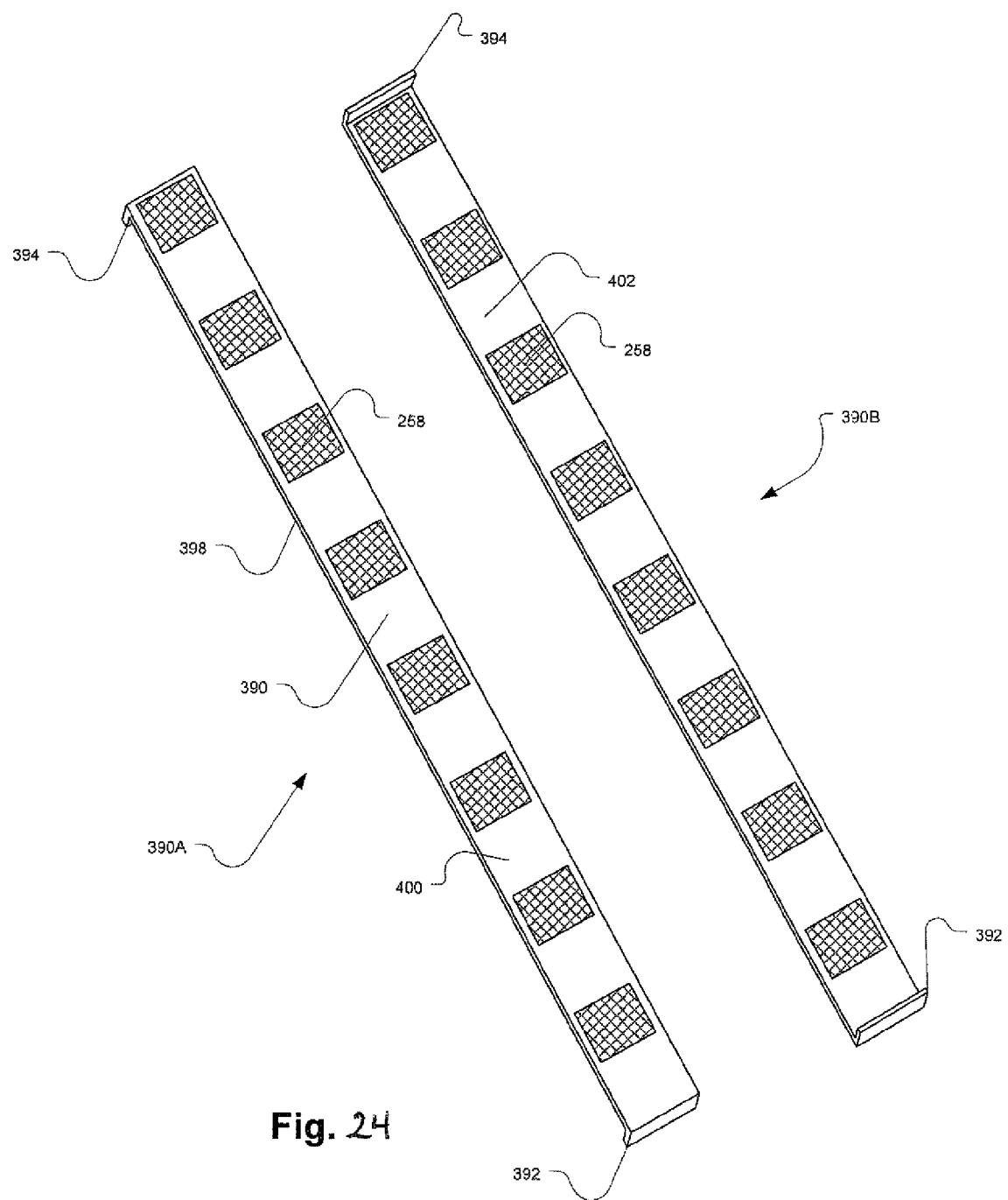
FIG. 24 illustrates perspective views of the substrate carrier of FIG. 23.

FIG. 24 shows the bar 398 of the substrate carrier 390 of FIG. 23 in two schematic perspective views 390A and 390B to better illustrate the structure of the bar 398. In the view 390A, the screenings 258 are facing up similar to that illustrated by FIG. 23 where the legs 392 and 394 are facing down and are placed on the collimator 102 along the row 256 when the screenings 258 on the surface 400 of the bar 398 are facing up and placed on top of the radiation-transparent substrate 390. Similarly, in the view 390B, the screenings 258 are facing down when the legs 392 and 394 are facing up and the radiation transparent material is placed on top of the screenings 258, which are viewed via the bar 398 and the surface 402. The screenings 258 may be, for example, glued to the surface 400 of the substrate 390 or pressed to be indented into surface 400. The screenings 258 are made from radiation-blocking materials, such as lead (Pb) or tungsten (W) and have thicknesses ensuring that most of the ionizing radiation used for the imaging is absorbed in the screenings 258.

The large size of the screenings 258 that is even larger than the pitch 2 of the collimator 102 is needed to improve the image reconstruction since the large screenings 258 produce better collimation of the solid scanning angles. As described above, better image reconstruction may be achieved since the large screenings 258 better ensure that there will be no overlapping between the scanning angles and that no scanning angles will contain another scanning angle and, thus, no repetitive information is produced during the scan.

However, the screenings 258 that are larger than the pitch of the collimator 102 have columns 108 that are adjacent to other columns 108 which have the large screenings 258 and may have no screenings 258. In such a case, the columns 108 that have no screenings 258 there above produce a forward-looking scan with high sensitivity.

Figure 25:
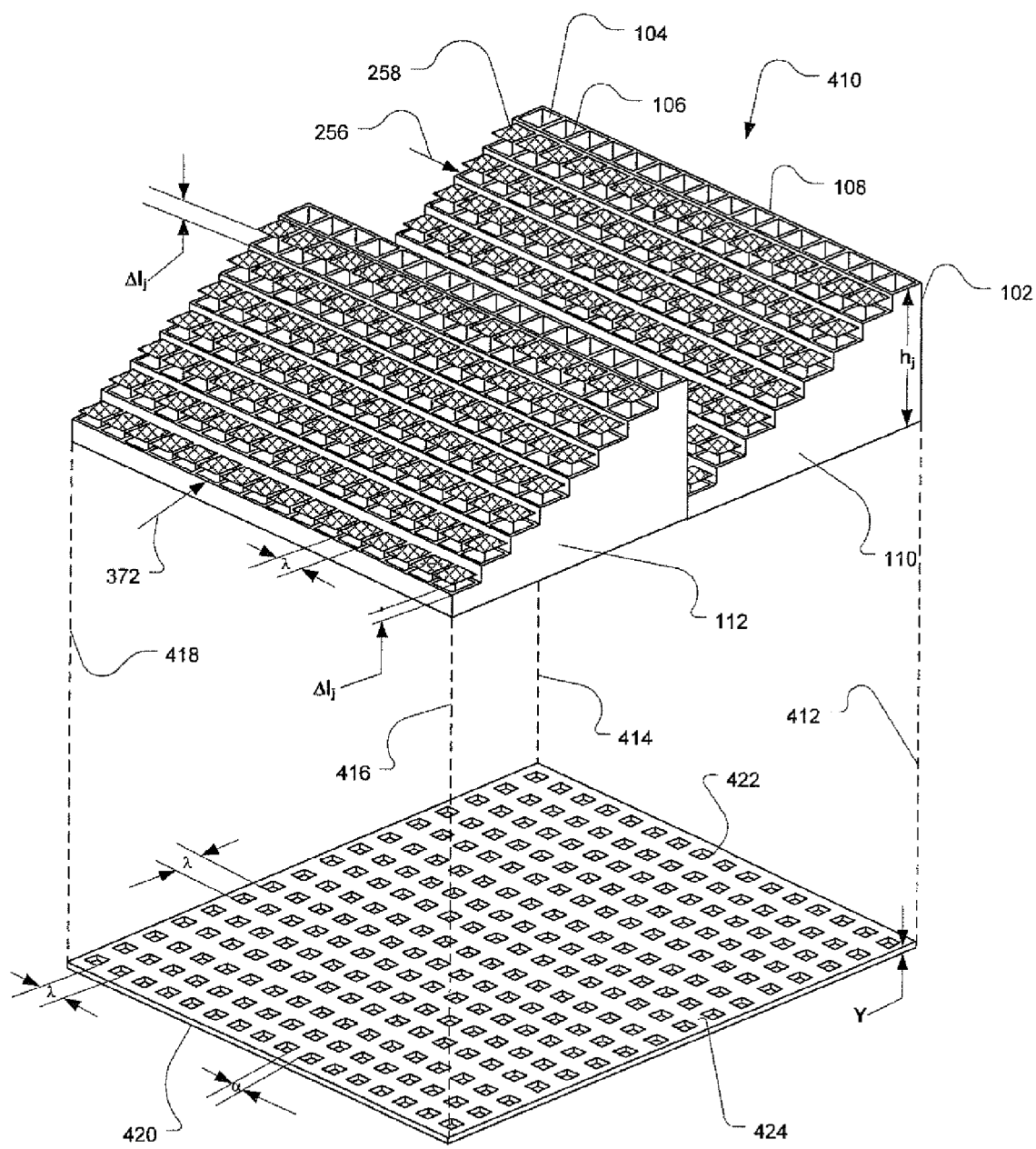
FIG. 25 is a schematic illustration of screenings of a collimator in accordance with another embodiment.

FIG. 25 schematically illustrates a configuration 410 which is an alternative configuration to the configuration 380 of FIGS. 20 and 21 which includes the screenings 258 that are larger than the pitch λ of the collimator 102. The configuration 410 of FIG. 25 has the advantages of the large screenings 258 of the configuration 380 without the disadvantages that may be associated with the configuration 380. Even though the configuration 410 includes the screenings 258 that are no larger than the pitch λ of the collimator 102, the configuration 410 still produces scanning angles that do not overlap each other and do not contain each other. Because the size $Z_j$ of screenings 258 is not larger than the pitch λ of the collimator 102, this allows placing the screenings 258 above any desired column 108 of the collimator 102. This eliminates from the configuration 380, the columns 108 that are adjacent to the columns 108 having the screenings 258 there above, which should have no screenings 258 there above.

FIG. 25 schematically illustrates the configuration 410 including two parts out of three parts of the collimator 102 as shown in FIGS. 2-7, which have the columns 108 arranged in eight groups along the rows 256 according to the heights of the columns 108 in each group. The heights $h_j$ of the groups arranged along the rows 256 are varied along the lines 372. The columns 108 have the opening D and are separated by the septa 106. The collimator 102 contains the parts 110 and 112 in the periodic structure of collimator 102, which includes the columns 108 having the screenings 258 there above except for the group of columns 108 having the highest height $h_j$. This group produces the narrowest scanning angle which cannot contain other scanning angles and, thus, does not need to have the screenings 258. The height differences $\Delta l_j$ between the screenings 258 and the edges of the columns 108 may be different for each group of the columns 108 and may be selected as desired.

A plate 420 of square pinholes 422 is positioned underneath the collimator 102 and in the close proximity to the collimator 102. The plate 420 is schematically illustrated as being remote from the collimator 102 for the clarity of the drawing and to allow illustrating the array structure of the square pinholes 422 without blocking the view thereof by the collimator 102 as would occur if the plate 420 were illustrated in close vicinity to the collimator 102 as actually positioned.

The square pinholes 422 having opening α and are arranged in a 2D array like a matrix having a 2D pitch λ. The lines 412, 414, 416 and 418 schematically illustrate the projection of the collimator 102 onto the plane 424 of the pinhole plate 420. The columns 108 of the collimator 102 and the pinholes 422 of the plate 420 both have the same 2D pitch λ in the illustrated embodiment. The center of each opening 104 of the columns 108 is aligned with the center of each pinhole 422 in the plate 420. Similar to the screenings 258, the thickness Y of the plate 424 and the material that it is made from are selected to ensure, in various embodiments, that most of the ionizing radiation used for the imaging is absorbed in the plate 420. Only the radiation that propagates through the pinholes 422 is collected by the detector 124 (shown in FIGS. 1 and 26 but, is not shown in FIG. 25).

Figure 26:
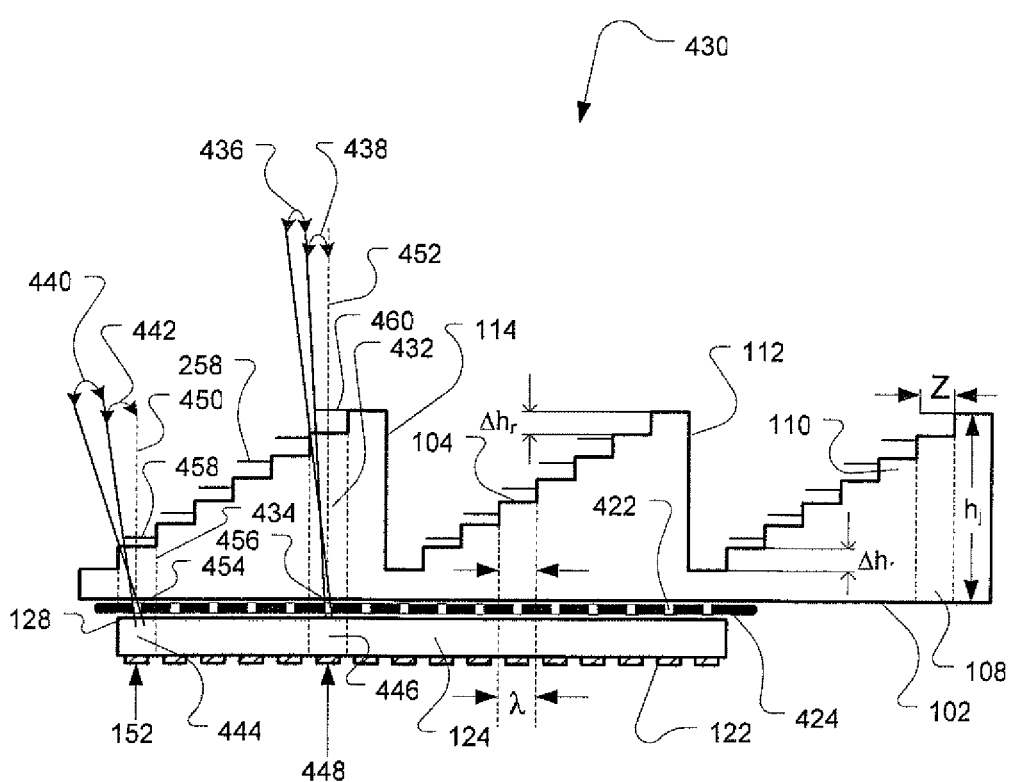
FIG. 26 is a schematic illustration of a side view cross-section of the collimator of FIG. 25.

FIG. 26 is a schematic illustration 430 of a side-view cross-section of the configuration 410 illustrated by FIG. 25 in perspective view showing the pinhole plate 424 in the proper position in close proximity underneath the collimator 102.

The configuration 430 shows the detector 124 (not shown in FIG. 25), which is positioned in close proximity under the plate 424.

The collimator 102 includes the periodic structure 110, 112 and 114 having the columns 108 and the screenings 258 above the openings 104 of the columns 108. The screenings 258 have a size $Z_j$ that is smaller than the 2D pitch λ which is the same for the columns 108 of the collimator 102, the pinholes 422 of the plate 424 and the pixels 122 of the detector 124. The heights $h_j$ of the columns 108, the height difference between the columns 108, such as the height differences $\Delta h_1$ and $\Delta h_n$, the distance $\Delta l_j$ of the screenings 258 from the edges of the columns 108, the size α of the square pinholes 422, the size $Z_j$ of the screenings 258 and the relative positions between the collimator 102, the plate 424 and the detector 124 are all selected to ensure that, in various embodiments, the scan of the configuration 430 will not produce repetitive information during the radiation-scan of the collimator 102. In other words, the parameters described above are selected to ensure that, in various embodiments, the solid scanning angles, such as the angles 440 and 436 which correspond to the same pixels 122 during different scanning steps for different scan positions of the collimator 102 when different heights $h_j$ of the columns 108 are positioned above the same respective pixels 122, will not contain or overlap each other. It should be noted that in some embodiments, the pitch of the pinholes is different than the pitch of the collimator. In some of these embodiments, the screenings are not provided.

Additionally, in some embodiments the pinholes (e.g., the pinholes 422) have the same aspect ratio with the pinhole plate providing additional spatial resolution and a degree of apodization to prevent multiplexing.

The tilted or inclination angles, such as the inclination angles 442 and 438 of solid scanning angles, such as the scanning angles 440 and 436 are measured relative to the lines 450 and 452, which are oriented normal to the imaging plane 128 of the detector 124, respectively. The solid scanning angle 440, which is the viewing scanning angle of the pixel 152 of the voxel 444 is produced by the column 434 of the columns 108, the pinhole 454 of the pinholes 422 and the screening 458 of the screenings 258. Similarly, the solid scanning angle 436, which is the viewing scanning angle of the pixel 448 of the voxel 446 is produced by the column 432 of the columns 108, the pinhole 456 of the pinholes 422 and the screening 460 of the screenings 258.

When the collimator 102 produces a scan by moving laterally step-by-step, a different column 108 having a different height $h_j$ is positioned, for each scanning step, above the pixel 122 of the detector 124 to produce different scanning angles. For example, in a certain scanning step when the column 434 of the columns 108 with the respective screening 458 of the screenings 258 is positioned above the pixel 152 of the pixels 122, this produces together with the pinhole 454 of the pinholes 422 the scanning angle 440 which is tilted by the angle 442 relative to the line 450 that is normal to the imaging plane 128. In another scanning step, when the column 432 of the columns 108 with the respective screening 460 of the screenings 258 is positioned above the pixel 152 of the pixels 122, this produces together with the pinhole 454 of the pinholes 422 the scanning angle 436 which is tilted by the angle 438 relative to the line 452 that is normal to imaging plane 128.

In another example similar to the above example, for a certain scanning step when the column 434 of the columns 108 with the respective screening 458 of the screenings 258 is positioned above the pixel 448 of the pixels 122, this produces together with the pinhole 454 of the pinholes 422 the scanning angle 440 which is tilted by the angle 442 relative to the line 450 that is normal to the imaging plane 128. In another scanning step when the column 432 of the columns 108 with the respective screening 460 of the screenings 258 is positioned above the pixel 448 of the pixels 122, this produces together with the pinhole 454 of the pinholes 422 the scanning angle 436 which is tilted by the angle 438 relative to the line 452 that is normal to the imaging plane 128.

The lateral movement of the collimator 102 produces a 2D angular scan of scanning angles, such as the scanning angles 440 and 436. To ensure that the scanning angles, such as the angles 440 and 436 when corresponding to the same pixels 122, during different scan steps of the collimator 102, will not contain or overlap each other, the following conditions are satisfied in various embodiments:

1. The scanning angles, such as the angles 440 and 436 should be collimated properly by the columns 108, the screenings 258 and the pinholes 422.
2. The angular rotation of the scanning angles, such as the angles 440 and 436, which is the change of the corresponding tilting angles 442 and 438 produced in response to the step-by-step lateral scan of the collimator 102 should be selected according to the variable collimations of scanning angles 440 and 436.
3. The change, between two next following scanning steps of the collimator 102, of inclination angles, such as the angles 442 and 438 that produce the angular scanning of the scanning angles, should be larger than the collimated scanning angles, such as the angles 440 and 436 corresponding to the scanning angles produced in the first scanning step out of the two next scanning steps.

It should be noted that is some embodiments, some redundant information may be acquired, for example, depending on a scanning time at a particular location.

The change of inclination angles, such as the angles 442 and 438 increases with the values of these angles, which means that this change increases with the size $Z_j$ of the screenings 258, the size D of the openings 104 and decreases with the height $h_j$ of the columns 108. Accordingly, for satisfying the conditions listed above, the inclination angle, such as the angle 438 of the highest column 108 which has the screening 258, such as the column 432, is the smallest inclination angle that the collimator 102 produces and should be large enough to satisfy the above listed conditions.

The plate 424 of the pinholes 422 is positioned relative to the collimator 102 and the pixels 122 of the detector 124 such that the centers of the pinholes 422, the openings 104 and the pixels 122 are all aligned with each other. The pinholes 422 of the plate 424 of the configuration 430 of FIG. 26 allows the pixels 122 to collect only radiation propagating from the radiation emitting object, such as the object 134 of FIG. 1, via the columns 108 of the collimator 102 and through the pinholes 422.

The centers of the pinholes 422 having relatively small size α are displaced laterally relative to the edges of the screenings 258 located above the openings 104 of the columns 108 of the collimator 102. Such displacements of the pinholes 422 relative to the edges of the screenings 258, increases the value of the tilting angles, such as the angles 442 and 438, of the scanning angles, such as the angles 440 and 436, respectively.

Increasing the inclination angle, such as the angle 438, of the highest column 108 having the screening 258, such as the column 432, is one of the conditions described above to produce high image quality by satisfying the conditions for preventing the situation in which the scanning angles, such as the angles 440 and 436 may include or overlap each other. Accordingly it should be clear that the pinhole plate 424 contributes significantly to the image quality of the scan produced by the collimator 102 by increasing the inclination angles even of the angles of the highest columns 108 that have the screenings 258.

Even though the pinholes 422 of the plate 424 may have the relatively small opening α, the sensitivity of the scan unit illustrated by the configuration 430 is still high as follows:

1. The scanning angles produced by the lateral scanning of the collimator 102 create a 2D angular scan, which is equivalent to areas scan, such as the areas 312A, 314A, 316A, 318A, 320A, 322A, 324A and 326A of the scanned region 340 of FIG. 15. Each of the scanned areas 312A, 314A, 316A, 318A, 320A, 322A, 324A and 326A is much larger than the area scanned by a conventional collimator while still maintaining much better spatial resolution of the reconstructed image due to the high quality scan achieved by the use of, for example:
   a. variable collimation
   b. the screenings 258; and/or
   c. the pinhole plate 424.

Figure 27:
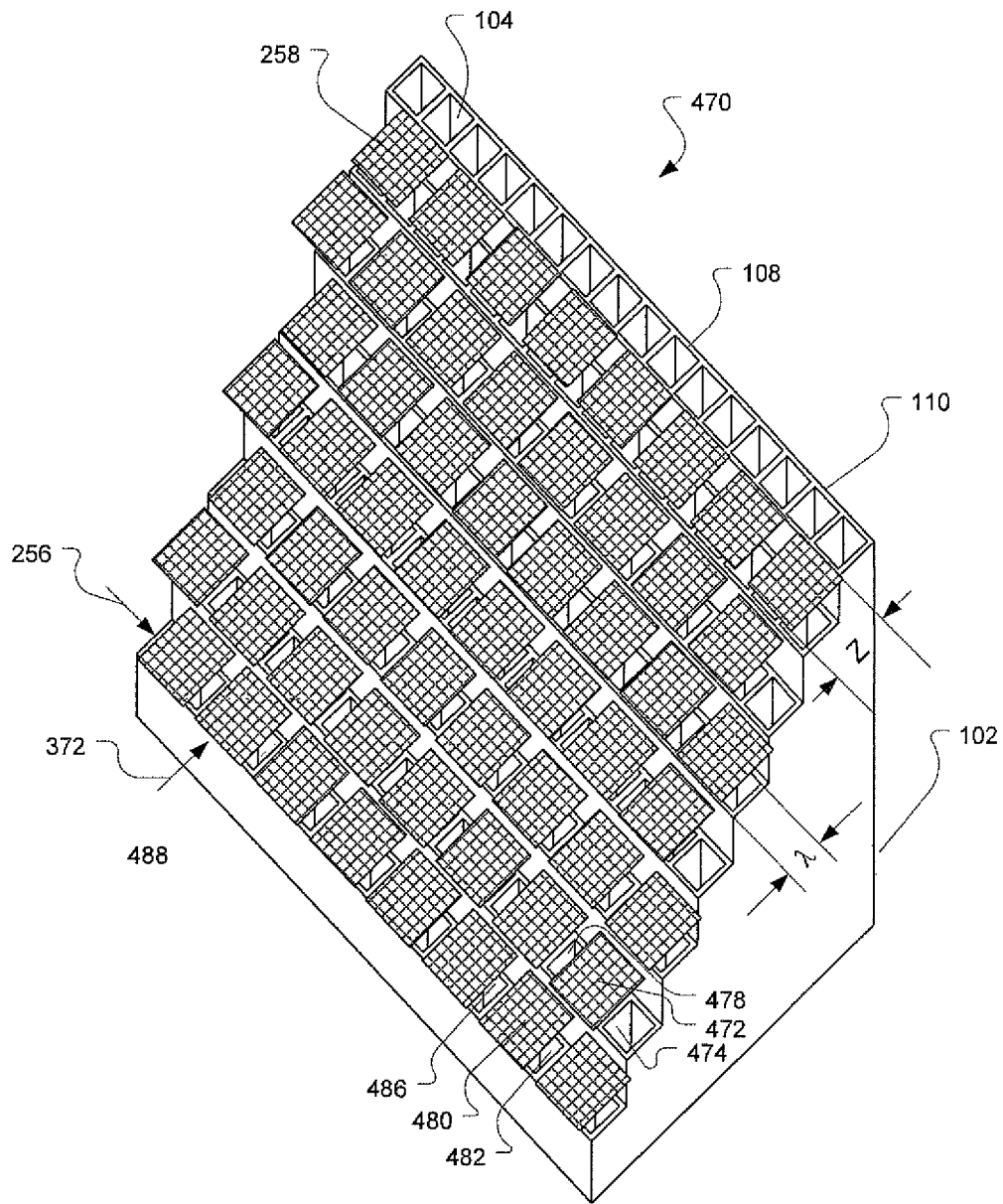
FIG. 27 is a schematic perspective illustration of a scan unit with a portion of a collimator having a periodic structure in accordance with another embodiment.
Figure 28:
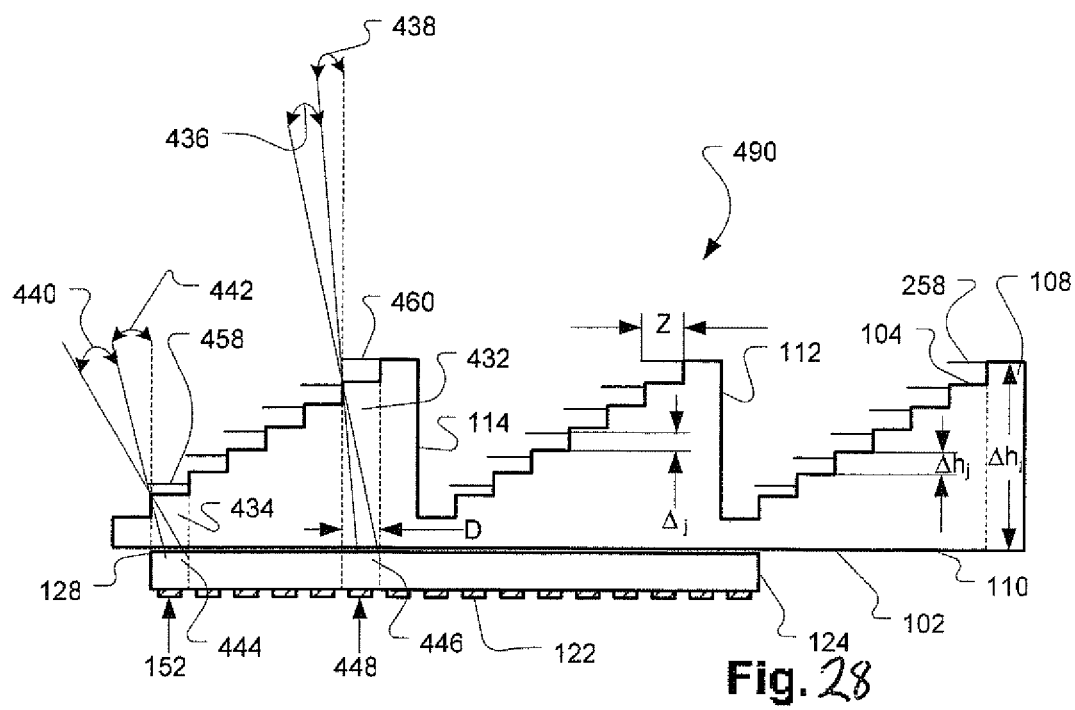
FIG. 28 is a schematic illustration of a cross-section side view of the scan unit of FIG. 27.
Figure 29:
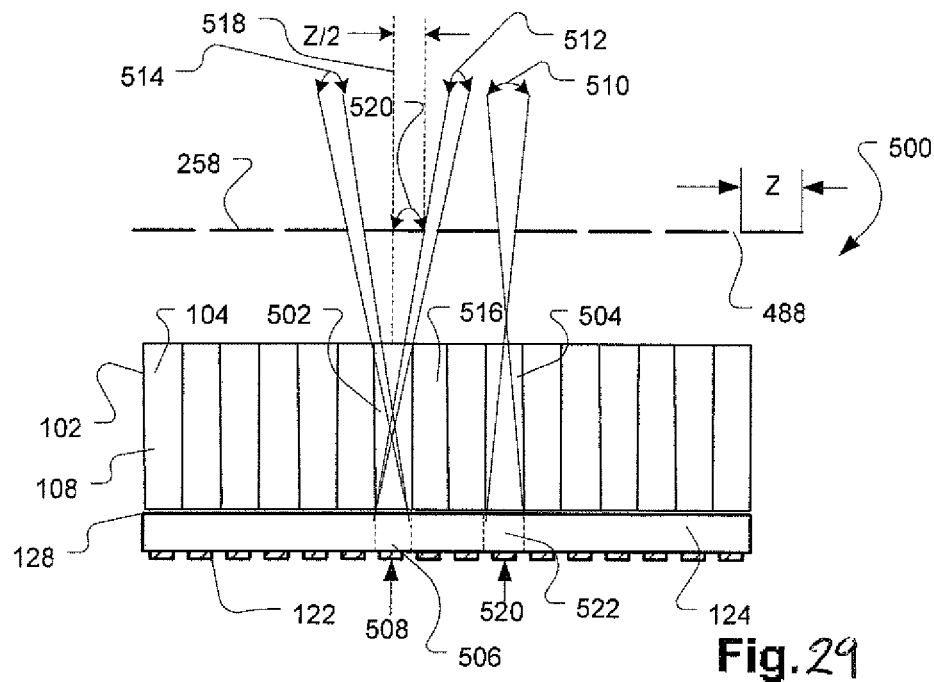
FIG. 29 is another schematic illustration of a cross-section side view of a group of columns of the scan unit of FIG. 27.

FIGS. 27-29 illustrate the scan units 470, 490 and 500 in perspective and side views, respectively, having an alternative configuration to the configuration 430 of FIG. 26. The scan unit 470 is configured to increase the inclination angle of the highest column 108 having the screening 258 based on the conditions above to produce high image quality by preventing the situation in which the scanning angles may include or overlap each other.

In particular, FIG. 27 illustrates the scan unit in the configuration 470 including the part 110 in the periodic structure of the collimator 102 having the columns 108 with the openings 104. The screenings 258 are placed above the columns 108, which are arranged in groups along the rows 256 according to height. The height change of the groups of columns 108 is varied in the direction of the lines 372. The columns 108 of the collimator 102 are arranged in an array form having a 2D pitch λ. The screenings 258 have a lateral size which is larger than the pitch λ. The scan unit 470 is similar to the scan unit 380 of FIG. 20 except that the size $Z_j$ of the screenings 258 of the unit 470 of FIG. 27 is significantly larger than the size $Z_j$ of the screenings 258 of FIG. 20.

The large size $Z_j$ of the screenings 258 of the scan unit 470 significantly increases the tilting angle of the scanning angle of the highest column 108 and brings this tilting angle into the range that is large enough to allow the removal of the pinhole plate, like the plate 424 used in the scan unit 430 of FIG. 26, which is used for the same purpose, i.e. increases significantly the tilting angle of the scanning angle of the highest column 108. The tilting angles of the scanning angles of the unit 470 are shown in detail in FIGS. 28 and 29.

The large size $Z_j$ of the screenings 258 that is significantly larger than the pitch λ results when the number of the screenings 258 is less than the number of columns 108. For example, the screening 478 in FIG. 27 is placed above the column 476 (not shown since the column 476 is under the screening 479), which is located between the columns 474 and 478 of the columns 108. Another example is the screening 480 that is placed above the column 484 (not shown since the column 484 is under the screening 478), which is located between the columns 482 and 486 of the columns 108.

Due to the large size $Z_j$ of the screenings 258, the screenings 258 cover completely the columns 108, wherein centers thereof are aligned with the centers of the screenings 258 and cover partially the columns 108 that are adjacent to the columns 108 that are completely covered by the screenings 258. Gaps 488 are formed between the screenings 258 in the regions above the columns 108 that are partially covered by the screenings 258.

FIG. 28 schematically illustrates a cross-section side-view 490 of the scan unit 470 shown in FIG. 27 cut along one of the lines 372 of the unit 470. The cross-section 490 is similar to the cross-section side view of the scan unit 430 of FIG. 26. The following changes to the scan unit 430 have been made to produce the scan unit 490:

1. The pinhole plate 424 is removed;
2. The detector 124 is moved towards the collimator 102; and
3. The size $Z_j$ of the screenings 258 is increased to be significantly larger than the 2D pitch λ of the columns 108 of the collimator 102 and the pixels 122 of the detector 124.

Accordingly, the same reference numerals are used to describe similar parts in the scan units 430 and 490 and the description for FIG. 26 is used to describe parts in the unit 430, which appear in the unit 490, and will not be repeated.

The heights $h_j$ of the columns 108, the height difference $\Delta h_j$ between the columns 108, the distance $\Delta l_j$ of the screenings 258 from the edges of the columns 108, the size of the screenings 258 and the relative positions between the collimator 102 and the detector 124 are all selected in various embodiments to ensure that the scan of the configuration 490 does not produce repetitive information during the radiation-scan of the collimator 102. In another words, the parameters mentioned above are selected to ensure, in various embodiments, that solid scanning angles such as the scanning angles 440 and 436 corresponding to the same pixels 122 during different scanning steps for different scan positions of the collimator 102 having different heights $h_j$ of the columns 108 are positioned above the same respective pixels 122, and will not contain or overlap each other.

The solid scanning angle 440, which is the viewing scanning angle of the pixel 152 of the voxel 444, is produced by the column 434 of the columns 108 and the screening 458 of the screenings 258. Similarly, the solid scanning angle 436, which is the viewing scanning angle of the pixel 448 of the voxel 446, is produced by the column 432 of the columns 108 and the screening 460 of the screenings 258.

When the collimator 102 produces a scan by moving laterally step-by-step, a different column 108 having different height $h_j$ is positioned, for each scanning step, above the pixel 122 of the detector 124 to produce different scanning angles. For example, in a certain scanning step when the column 434 of the columns 108 with the respective large screening 458 of the screenings 258 is positioned above the pixel 152 of the pixels 122, this produces together with the screening 458 the scanning angle 440 which is tilted by the angle 442 relative to the line 450 that is normal to the imaging plane 128. In another scanning step, when the column 432 of the columns 108 with the respective screening 460 of the screenings 258 is positioned above the pixel 152 of pixels 122, this produces together with the screening 460 the scanning angle 436 which is tilted by the angle 438 relative to the line 452 that is normal to the imaging plane 128.

In another example similar to the example above, for a certain scanning step when the column 434 of the columns 108 with the respective screening 458 of the screenings 258 is positioned above the pixel 448 of the pixels 122, this produces together with the screening 458 the scanning angle 440 which is tilted by the angle 442 relative to the line 450 that is normal to the imaging plane 128. In another scanning step when the column 432 of the columns 108 with the respective screening 460 of the screenings 258 is positioned above the pixel 448 of the pixels 122, this produces together with the screening 460 the scanning angle 436 which is tilted by the angle 438 relative to the line 452 that is normal to the imaging plane 128.

The lateral movement of the collimator 102 produces a 2D angular scan of scanning angles, such as the scanning angles 440 and 436. In various embodiments, to ensure that scanning angles, such as the angles 440 and 436 when related to the same pixels 122, during different scan steps of the collimator 102, will not contain or overlap each other, the following conditions are satisfied:

1. The scanning angles, such as the angles 440 and 436 are collimated properly by the columns 108 and the large screenings 258.
2. The angular rotation of the scanning angles, such as the angles 440 and 436, which is the change of the corresponding tilting angles 442 and 438 produced in response to the step-by-step lateral scan of the collimator 102, is selected according to the variable collimations of the scanning angles 440 and 436.
3. The change, between the scanning steps of the collimator 102, of inclination angles, such as the angles 442 and 438 that produce the angular scanning of the scanning angles, are larger than the collimated scanning angles, such as the angles 440 and 436 corresponding to the scanning angles produced in the previous scanning step.

The change of inclination angles, such as the angles 442 and 438, increases with the values of these angles, which means that this change increases with the size $Z_j$ of the screenings 258 and decreases with the height $h_j$ of the columns 108. Accordingly, for satisfying the conditions above, in various embodiments, the inclination angle, such as the angle 442 of the highest column 108 which has the screening 258, such as the column 432 is the smallest inclination angle that the collimator 102 produces and should be large enough to satisfy the conditions.

When the size of the screenings 258 is large, the edges of the screenings 258 are largely displaced laterally relative to the openings 104 of the columns 108 of the collimator 102. Such large displacements between the openings 104 of the columns 108 and the edges of the screenings 258, increases the value of the tilting angles, such as the angles 442 and 438, of scanning angles, such as the angles 440 and 436, respectively.

Increasing the inclination angle, such as the angle 442, of the highest column 108 having the screening 258, such as the column 432, is one of the conditions described above to produce high image quality by satisfying the conditions for preventing the situation in which the scanning angles, such as the angles 440 and 436 may include or overlap each other.

Accordingly, it should be clear that the large size $Z_j$ of the screenings 258 contributes significantly to the image quality of the scan produced by the collimator 102 by increasing the inclination angles, even of those of the highest columns 108 that have the screenings 258.

Even with the screenings 258 being large, the sensitivity of the scan unit illustrated by the configuration 490 is still high as follows:

1. The scanning angles produced by the lateral scanning of the collimator 102 create the 2D angular scan, which is equivalent to the area scan, such as the areas 312A, 314A, 316A, 318A, 320A, 322A, 324A and 326A of the scanned region 340 of FIG. 15. Each of the scanned areas 312A, 314A, 316A, 318A, 320A, 322A, 324A and 326A is much larger than the area scanned by a conventional collimator while still maintaining much better spatial resolution of the reconstructed image due to the high quality scan achieved by the use of:
   a. variable collimation; and
   b. the screenings 258.

FIG. 29 schematically illustrates a cross-section side-view 500 of a group of columns of the scan unit 470 shown in FIG. 27 cut along one of the rows 256 of the unit 470 which includes the columns 108 having the same height $\Delta h_j$ and are related to one group of the eight groups that each of the periodic structures 110, 112 and 114 of the collimator 102 contain. The group of columns 108 shown in FIG. 29 is the group with the highest height $h_j$ that have the screening 258.

FIGS. 28 and 29 illustrate side cross-section views 490 and 500 of the same scan unit 470 of FIG. 27 cut along the line 372 and the row 256, respectively. However, FIGS. 28 and 29 are illustrated with different magnifications and are only schematic illustrations that may not be proportional to each other.

FIG. 29 shows the side-view cross section 500 of the unit 470 of FIG. 27 illustrating the large screenings 258 having the size 4 above the collimator 102. The screenings 258 are centered above part of the columns 108, such as the column 502 and the gaps 488 between the screenings 258 are centered above the columns 108, such as the column 516 adjacent to the columns 108, such as the column 502 that the screenings 258 are centered above. The columns 108 are placed above the imaging plane 128 of the detector 124 having the pixels 122 such as the pixels 508 that the column 502 is placed above and above the voxel 506.

The displacement between the edge of the screenings 258 and the centers of the openings 104, such as the center 518 to which the centers of the screenings 258 are aligned is equal to $Z_j/2$. The size $Z_j$ of the screenings 258 is provided to create the displacement 42 to ensure that the inclination angles, such as the angle 520 of scanning angles, such as the angles 512 and 514, produce, even for the highest column 108 in the collimator 102, radiation scanning with high quality in accordance with various embodiments and as described herein.

The viewing angle 510 is the scanning solid angle of the pixels 520 and the voxel 522. The scanning angle 510 is a forward looking angle. Accordingly, the scan unit 470 of FIG. 27 is a combination of the columns 108, a portion of which producing a forward looking scan with angles such as the scanning angle 510 and the remaining columns 108 producing a non-forward looking scan with angles such as the angles 512 and 514. This combination may be optimized in various embodiments for achieving high image quality together with high sensitivity as described in connection with FIG. 19.

It should be noted that while various embodiments describe moving the collimator relative to the detector, variations and modifications are contemplated. For example, in some embodiments, the collimator and detector may be moved relative to the object, such as the patient. For example, each pinhole of a pinhole plate images multiple bores of the collimator, such that a particular image voxel is viewed through multiple pinholes resulting in multiple pinhole projections. In various embodiments, the amount of overlapping of the pinhole projections may be changed or varied when the length of the bores is changed. Accordingly, by moving the pinholes (forming part of the collimator) with the detector closer to or farther away from the object, the amount of pinhole projection overlap is changed. For example, as the length of the bore is made shorter or longer, more or less overlapping of the projections results.

Figure 30:
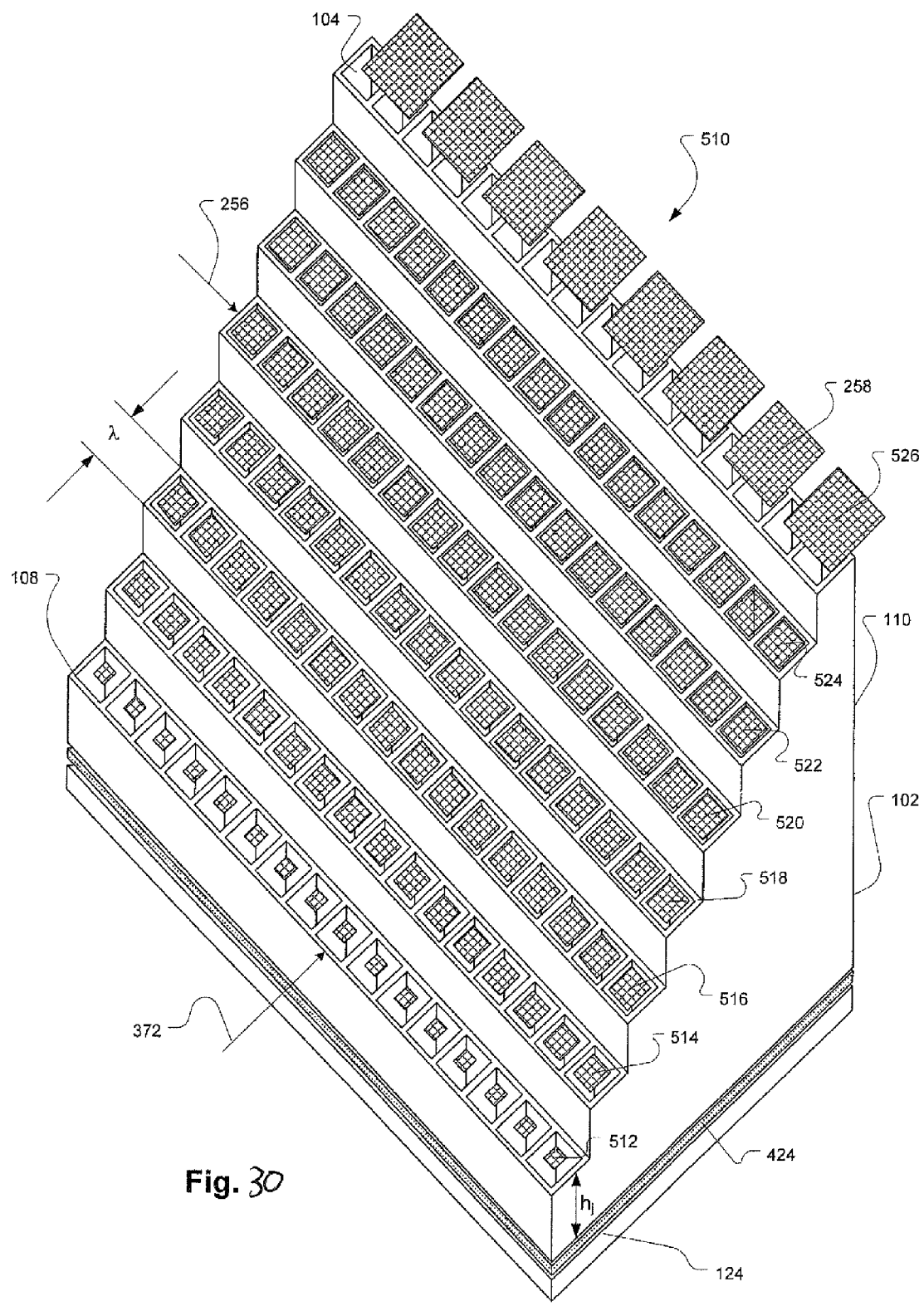
FIG. 30 is a schematic perspective illustration of a scan unit with a portion of a collimator having a periodic structure in accordance with another embodiment.

FIG. 30 is a schematic illustration of a scan unit 510 including the part 110 in the periodic structure of the collimator 102. The columns 108 having the openings 104 are arranged according to height $h_j$ in eight groups arranged along the rows 256. The heights of the groups of columns 108 are varied along the lines 372. Each group of the columns 108 may have the screenings 258 with different size $Z_j$ selected from the screening types 512, 514, 516, 518, 520, 522, 524 and 526.

The screenings 258 are supported by a radiation transparent substrate (not shown) positioned on top of the collimator 102.

Since part of the columns 108 have a size $Z_j$ that is smaller than the 2D pitch $\lambda$ of the columns 108 of the collimator 102, the pinhole plate 424 may be inserted between the collimator 102 and the radiation detector 124 to improve the image produced by scan unit 510 described above in connection with FIG. 26.

It should be noted that while the various embodiments illustrate pinhole-arrays having square pinholes, it should be appreciated the pinholes may have different shapes, such as, slits and or circular pinholes. Also, while the screenings 258 are shown in some of the embodiments as being attached to the columns 108, the screenings 258 may be supported by radiation transparent substrates placed on the collimator 102, such as the substrates 350 and 390 illustrated by FIGS. 18 and 24. Further, while the screenings 258 in some embodiments are illustrated without supporting radiation transparent substrates, it should be appreciated that the substrates are not shown to reduce the amount of parts shown in the drawings for clarity. Additionally, while in some embodiments the collimator 102 is illustrated as having one periodic structure, it should be appreciated that the number of periodic structures in the collimator 102 can be selected as desired and the collimator 102 in some embodiments may be larger than the detector 124 by one periodic structure.

In some embodiments, while one scan unit is illustrated, it should be appreciated that multiple scan unites positioned in multiple viewing angles of the emitting object 134 may be used in multiple camera-heads to produce SPECT and 3D imaging. Also, while in some embodiments the pinhole-plate 424 is illustrated as being static above the detector 124 when the collimator 102 moves laterally above the plate 424, it should be appreciated that the plate 424 may move together with the collimator 102 and may be attached to the collimator 102.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A scan unit for scanning and collecting ionizing radiation emitted from a radiation emitting object, the scan unit comprising:
   an array of at least one pixelated radiation detector having an imaging surface including a two-dimensional (2D) array of pixels; and
   a collimator positioned between the radiation detector and the radiation emitting object, the collimator including a 2D array of columns having openings and septa forming bores, wherein the columns are arranged in groups along rows of the 2D array of columns, and the bores within one of the groups having a different aspect ratio than the bores in another one of the groups, wherein the collimator includes a plurality of periodic structures, each of the periodic structures containing the columns that are arranged in groups along rows of the 2D array of columns.

2. The scan unit of claim 1, wherein the array of columns of the collimator have a same pitch.

3. The scan unit of claim 1, wherein the columns in each group have a group-height that is different from a group-height of other groups of the columns, the group-height being a height for the bores in the group.

4. The scan unit of claim 3, wherein the group-height is varied in a direction along lines of the array of columns.

5. The scan unit of claim 1, wherein projections of centers of the openings and septa of the columns onto the imaging surface are aligned with centers of the pixels and border-lines between adjacent pixels, respectively, to produce radiation paths from the object to the pixels of the detector via the collimator.

6. The scan unit of claim 1, further comprising a motor, wherein the motor is configured to move the collimator linearly, by scanning steps, in a direction along the lines of the array of the columns and parallel to the imaging surface of the detector for changing relative positions between the groups of the columns and the pixels.

7. The scan unit of claim 6, wherein a size of the scanning steps is equal to a pitch size of the array of columns.

8. The scan unit of claim 6, wherein for each relative position of the relative positions and for each pixel of the pixels in each scanning step of the steps, a column with a different group-height is positioned above each pixel for changing radiation paths by changing the relative positions.

9. The scan unit of claim 1, wherein the radiation detector is configured for Single Photon Emission Computed Tomography (SPECT) imaging.

10. The scan unit of claim 1, wherein the bores are parallel to each other.

11. The scan unit of claim 1, further comprising one or more screenings coupled to the columns to restrict radiation paths to the radiation detector.

12. The scan unit of claim 11, wherein the one or more screenings are configured to prevent forward looking scanning solid angles of the collimator.

13. The scan unit of claim 1, wherein a quantity of the bores is greater than a quantity of the pixels in the 2D array of pixels.

14. A scan unit for scanning and collecting ionizing radiation emitted from a radiation emitting object, the scan unit comprising:
a plurality of scanning elements; and
a variable collimation system, wherein for each of a plurality of collimation and directional settings of the plurality of scanning elements there is a corresponding two-dimensional (2D) scanning angle for acquiring data to generate an image that is different for different scanning angles, wherein the scanning angles of the plurality of scanning elements are different from each other based on heights of bores formed by a collimator, wherein the scanning angles are further based on screenings coupled to the collimator.

15. The scan unit of claim 14, wherein a lateral scan of the variable collimation system is converted into a 2D radiation scan.

16. The scan unit of claim 14, wherein the variable collimation system is configured to produce variable collimation by lateral displacement.

17. The scan unit of claim 14, wherein the acquired data includes data for producing substantially different images for the different scanning angles.

18. The scan unit of claim 14, wherein the collimator is positioned between the radiation detector and the radiation emitting object, the collimator including a 2D array of columns having openings and septa forming the bores, wherein the columns are arranged in groups along rows of the 2D array of columns, and the bores within one of the groups having a different aspect ratios than the bores in another one of the groups.

19. A method for scanning and collecting ionizing radiation emitted from an object using a scan unit having an array of at least one pixelated radiation detector with an imaging surface including a two-dimensional (2D) array of pixels, the method comprising:
configuring a collimator to be positioned between the radiation detector and the radiation emitting object, the collimator including a 2D array of columns having openings and septa forming bores, wherein the columns are arranged in groups along rows of the 2D array of columns, and the bores within one of the groups having a different aspect ratio than the bores in another one of the groups; and
controlling the collimator to move linearly, by scanning steps, in a direction along the lines of the array of the columns and parallel to the imaging surface of the detector for changing relative positions between the groups of the columns and the pixels, wherein for each relative position of the relative positions and for each pixel of the pixels in each scanning step of the steps, a column with a different group-height is positioned above each pixel for changing radiation paths by changing the relative positions.

20. The method of claim 19, wherein a size of the scanning steps is equal to a pitch size of the array of columns.

21. The method of claim 19, further comprising controlling the collimator to perform Single Photon Emission Computed Tomography (SPECT) imaging.

* * * * *